US009186152B2

(12) United States Patent
Campbell et al.

(10) Patent No.: US 9,186,152 B2
(45) Date of Patent: Nov. 17, 2015

(54) LEFT ATRIAL APPENDAGE OCCLUSIVE DEVICES

(75) Inventors: Benjamin D. Campbell, Flagstaff, AZ (US); Edward H. Cully, Flagstaff, AZ (US); Jeffrey B. Duncan, Flagstaff, AZ (US); Nichlas L. Helder, Flagstaff, AZ (US); Coby C. Larsen, Flagstaff, AZ (US); Steven J. Masters, Flagstaff, AZ (US); Scot K. Mathena, Flagstaff, AZ (US); Thomas R. McDaniel, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/293,803

(22) Filed: Nov. 10, 2011

(65) Prior Publication Data

US 2012/0172927 A1    Jul. 5, 2012

Related U.S. Application Data

(60) Provisional application No. 61/413,253, filed on Nov. 12, 2010, provisional application No. 61/413,649, filed on Nov. 15, 2010, provisional application No. 61/535,888, filed on Sep. 16, 2011.

(51) Int. Cl.
*A61B 17/03*   (2006.01)
*A61B 17/12*   (2006.01)
*A61B 17/00*   (2006.01)

(52) U.S. Cl.
CPC .......... *A61B 17/1215* (2013.01); *A61B 17/0057* (2013.01); *A61B 17/12122* (2013.01); *A61B 17/12145* (2013.01); *A61B 17/12172* (2013.01); *A61B 2017/00592* (2013.01); *A61B 2017/00597* (2013.01); *A61B 2017/00615* (2013.01); *A61B 2017/00623* (2013.01); *A61B 2017/00632* (2013.01); *A61B 2017/1205* (2013.01)

(58) Field of Classification Search
CPC .................... A61B 17/0057; A61B 17/12122; A61B 17/12145; A61B 17/1215; A61B 17/12172; A61B 2017/00592; A61B 2017/00597; A61B 2017/00615; A61B 2017/00623; A61B 2017/00632; A61B 2017/1205
USPC .......................................... 606/151, 200, 213
See application file for complete search history.

(56) References Cited

U.S. PATENT DOCUMENTS

| 4,138,939 A | * | 2/1979 | Feld ................................ 99/418 |
| 4,425,908 A | | 1/1984 | Simon |
| 5,242,462 A | * | 9/1993 | El-Nounou et al. .......... 606/200 |
| 5,451,235 A | | 9/1995 | Lock et al. |

(Continued)

FOREIGN PATENT DOCUMENTS

| WO | 2008/153872 | 12/2008 |
| WO | 2009/029261 | 3/2009 |
| WO | 2012/163257 | 12/2012 |

*Primary Examiner* — Thomas McEvoy
*Assistant Examiner* — Julie A Szpira
(74) *Attorney, Agent, or Firm* — Katherine L. Carleton

(57) ABSTRACT

An occlusive device for left atrial appendage occlusion that has a membrane component configured to inhibit passage of blood and an expandable frame formed from a plurality of wires having a cupped occlusive component at least partially covered with the membrane component, one or more anchors with looped ends and a hub component. The occlusive device can be delivered percutaneously. The occlusive device is useful in the occlusion of the left atrial appendage.

50 Claims, 43 Drawing Sheets

(56) References Cited

U.S. PATENT DOCUMENTS

| | | | |
|---|---|---|---|
| 5,741,297 A * | 4/1998 | Simon | 606/213 |
| 5,861,003 A | 1/1999 | Latson et al. | |
| 5,976,174 A | 11/1999 | Ruiz | |
| 6,616,685 B2 * | 9/2003 | Rousseau | 606/213 |
| 6,689,150 B1 | 2/2004 | VanTassel et al. | |
| 7,011,094 B2 * | 3/2006 | Rapacki et al. | 128/207.15 |
| 7,044,134 B2 | 5/2006 | Khairkhahan et al. | |
| 7,582,104 B2 | 9/2009 | Corcoran et al. | |
| 2004/0138697 A1 * | 7/2004 | West | 606/200 |
| 2004/0143293 A1 | 7/2004 | Marino et al. | |
| 2005/0038470 A1 | 2/2005 | Van der Burg et al. | |
| 2006/0058832 A1 * | 3/2006 | Melzer et al. | 606/200 |
| 2006/0122646 A1 * | 6/2006 | Corcoran et al. | 606/213 |
| 2006/0122647 A1 | 6/2006 | Callaghan et al. | |
| 2007/0083230 A1 * | 4/2007 | Javois | 606/213 |
| 2007/0232992 A1 * | 10/2007 | Kutsko et al. | 604/30 |
| 2007/0244517 A1 | 10/2007 | Callaghan | |
| 2007/0293891 A1 * | 12/2007 | Corcoran et al. | 606/213 |
| 2009/0062838 A1 * | 3/2009 | Brumleve et al. | 606/198 |
| 2009/0112249 A1 | 4/2009 | Miles et al. | |
| 2009/0292310 A1 * | 11/2009 | Chin et al. | 606/215 |
| 2010/0228285 A1 | 9/2010 | Miles et al. | |
| 2010/0234878 A1 * | 9/2010 | Hruska et al. | 606/213 |
| 2010/0312270 A1 * | 12/2010 | McGuckin et al. | 606/200 |
| 2012/0065667 A1 | 3/2012 | Javois et al. | |

* cited by examiner

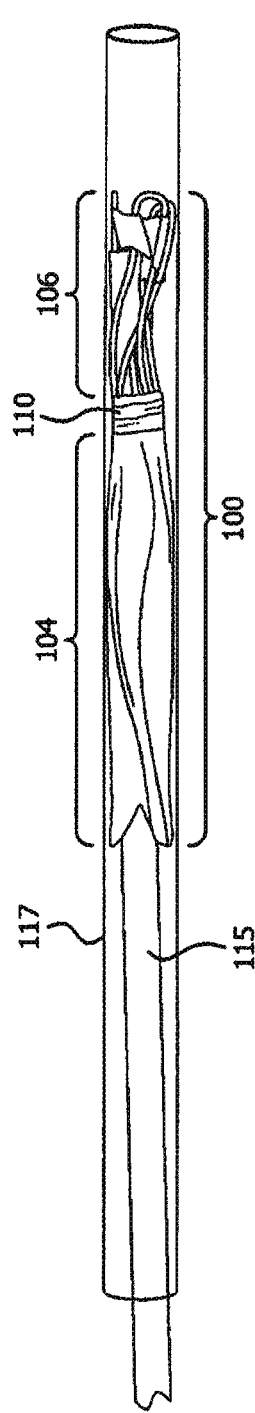
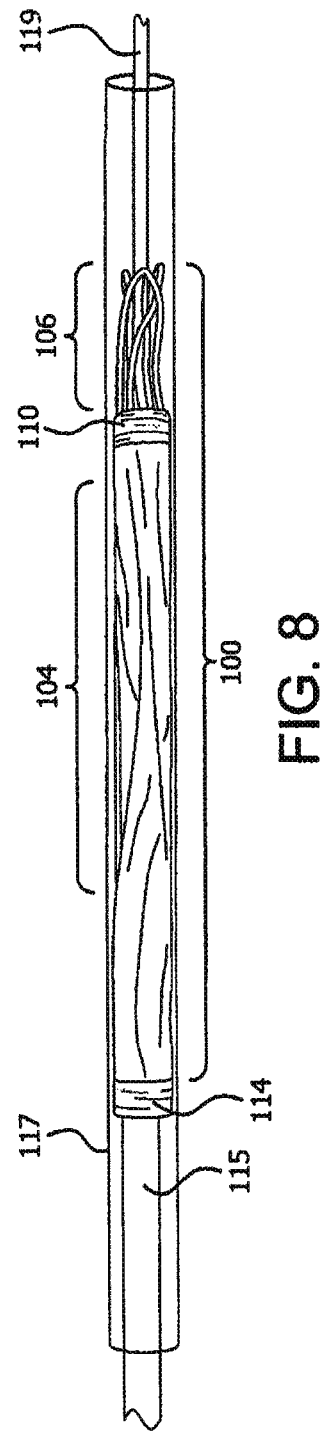
FIG. 7
FIG. 8

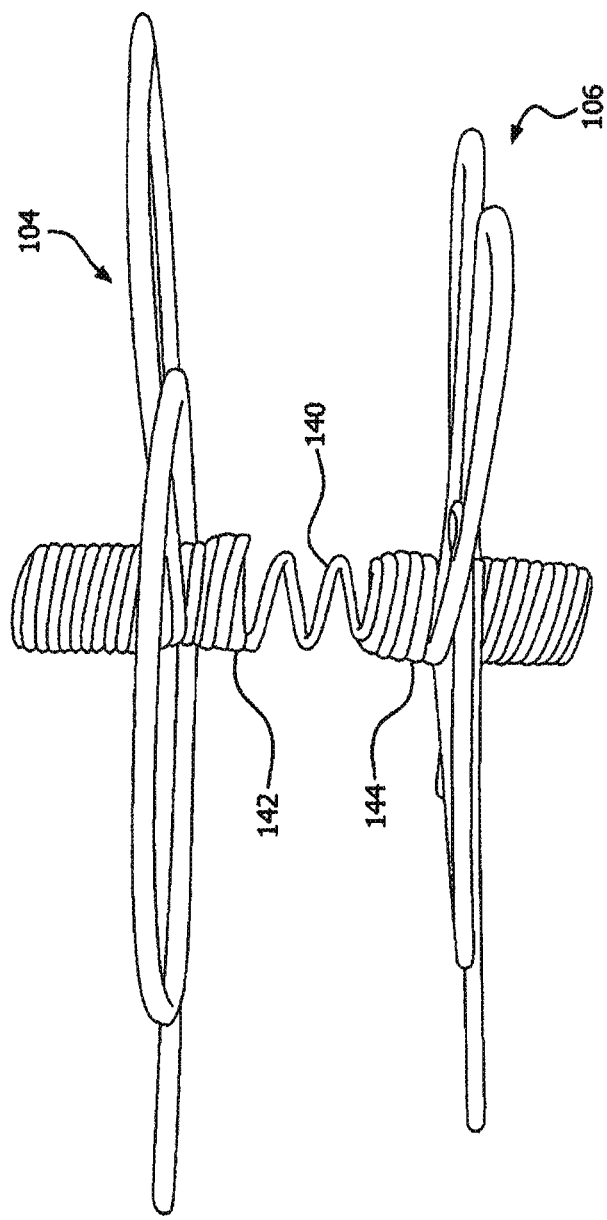

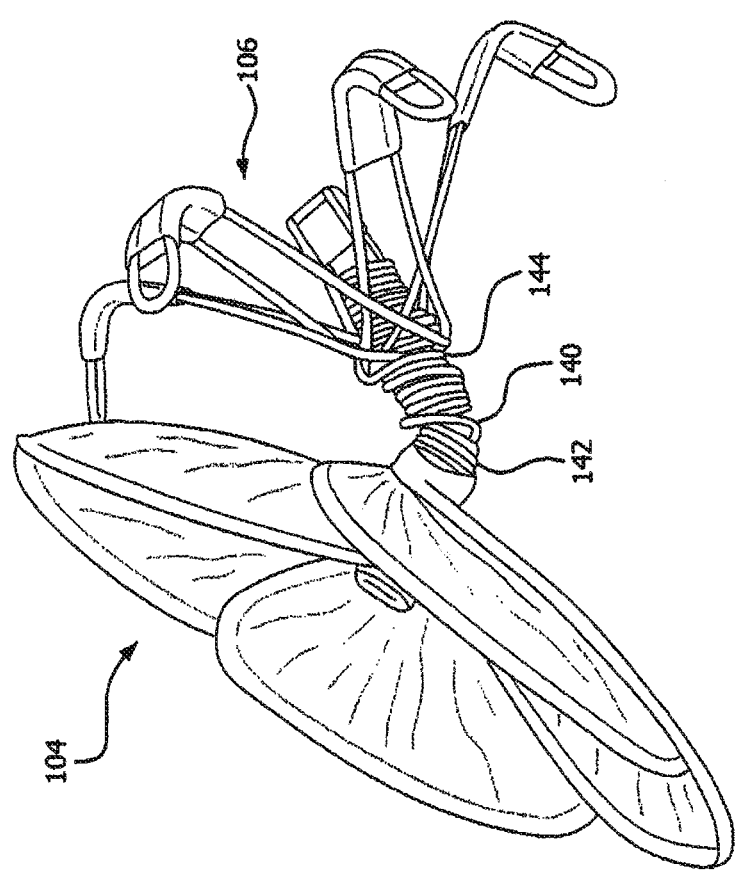

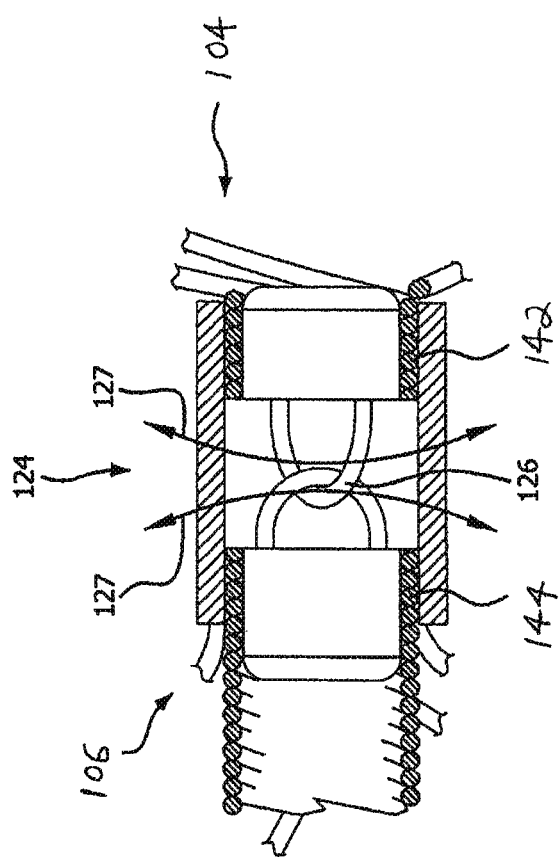

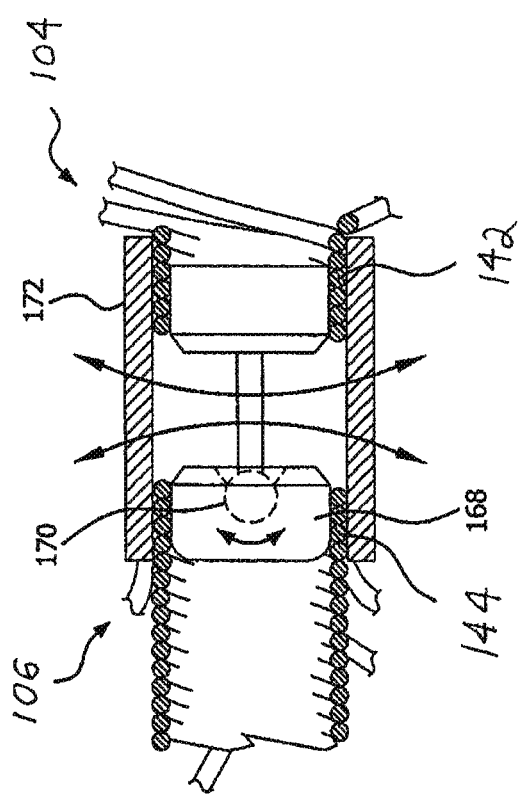

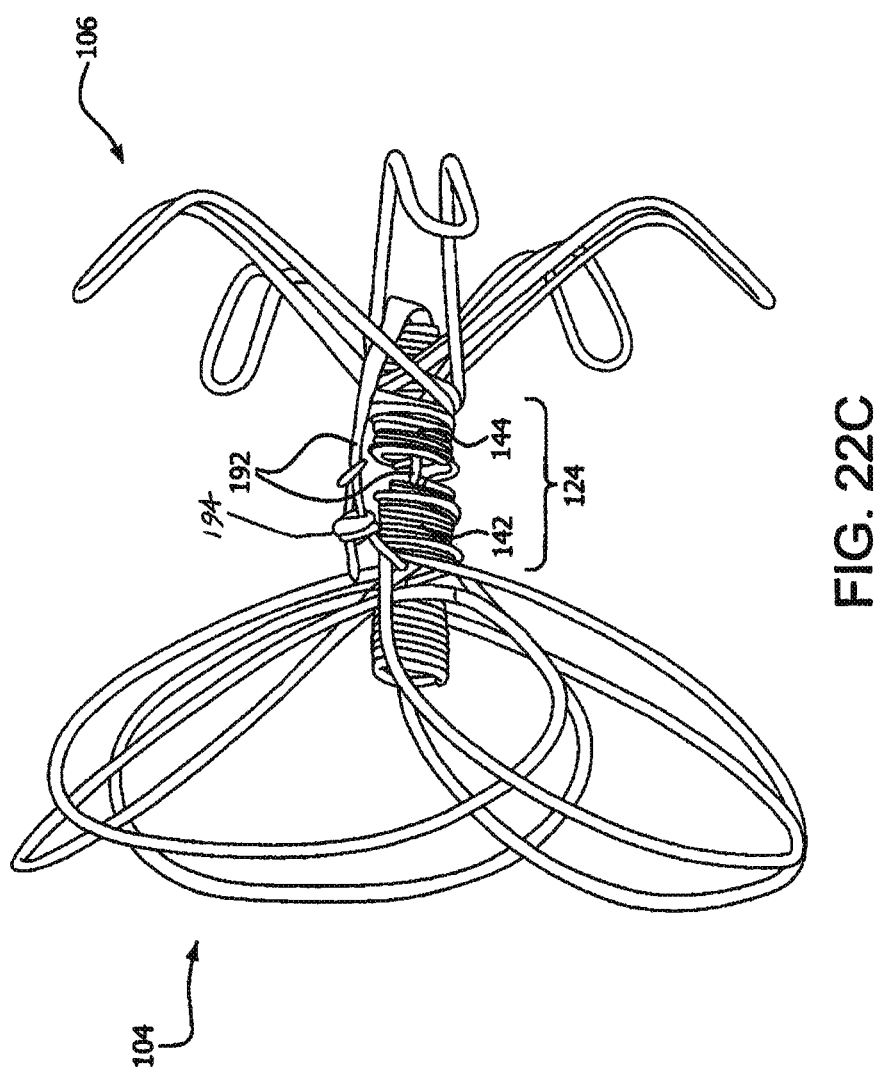

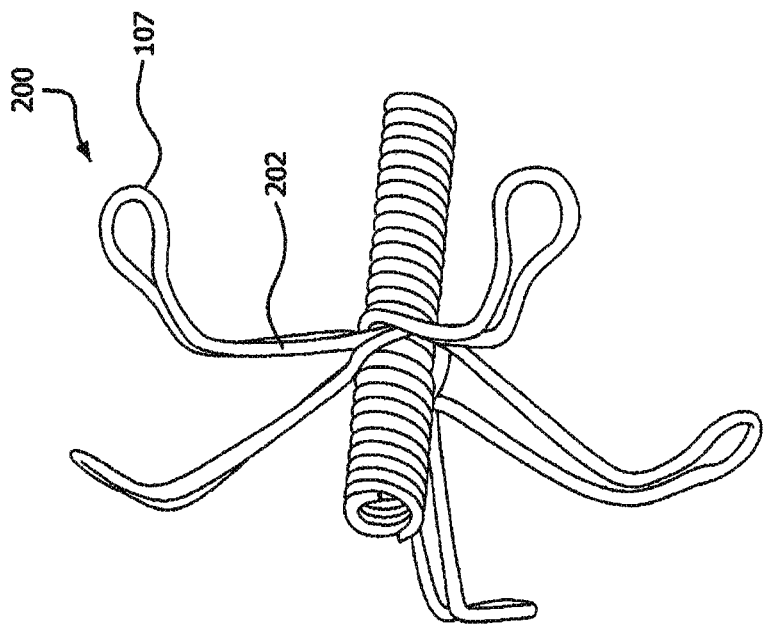

LEFT ATRIAL APPENDAGE OCCLUSIVE DEVICES

CROSS REFERENCE TO RELATED APPLICATIONS

The present application claims priority to U.S. Provisional Patent Application Ser. No. 61/413,253 filed Nov. 12, 2010; U.S. Ser. No. 61/413,649 filed Nov. 15, 2010; and U.S. Ser. No. 61/535,888 filed Sep. 16, 2011, each of which is incorporated by reference in its entirety.

FIELD OF THE INVENTION

The present invention relates to occlusive devices useful, for example, in occluding structures or conduits within a patient, particularly an atrial appendage in the human heart. Devices of the present invention can be delivered percutaneously or in an endovascular fashion.

BACKGROUND OF THE INVENTION

Embolic stroke is the nation's third leading killer, and is a major cause of disability. There are over 780,000 strokes per year in the United States alone. Of these, roughly 110,000 are hemorrhagic, and 670,000 are ischemic (either due to vessel narrowing or to embolism). The most common cause of ischemic stroke of cardiac origin is thromboemboli due to atrial fibrillation. One out of every six strokes (approximately 130,000 per year) is attributed to atrial fibrillation. Atrial fibrillation is the most common heart arrhythmia; it results in a rapid and chaotic heartbeat that lowers cardiac output and leads to irregular and turbulent blood flow in the vascular system. There are over eight million people worldwide with atrial fibrillation, with about eight hundred thousand new cases reported each year. Atrial fibrillation is associated with a 500 percent greater risk of stroke compared with age-matched healthy controls. A patient with atrial fibrillation typically has a significantly decreased quality of life due, in part, to the fear of stroke, and the pharmaceutical regimen necessary to reduce that risk.

When patients develop atrial thrombus from atrial fibrillation, the clot occurs in or originates from the left atrial appendage (LAA) of the heart over ninety percent of the time. The left atrial appendage is a closed cavity which looks like a small thumb or windsock; it is connected to the anterolateral wall of the left atrium between the mitral valve and the root of the left pulmonary vein. The left atrial appendage contracts with the left atrium during a normal heart cycle, thus keeping blood from becoming stagnant. However, with atrial fibrillation, the left atrial appendage often fails to contract with any vigor due to the disorganized electrical signals. As a result, thrombus formation is predisposed to form in the stagnant blood within the left atrial appendage.

Pharmacological therapies for stroke prevention in atrial fibrillation patients such as oral or systemic administration of warfarin have often been inadequate due to serious side effects and lack of patient compliance. Invasive surgical or thorascopic techniques have been used to obliterate the left atrial appendage, however, many patients are not suitable candidates for such procedures due to compromised condition or previous cardiac surgery. In addition, the perceived risks of these surgical procedures often outweigh the potential benefits.

Many of the current commercial devices that attempt to occlude the left atrial appendage for stroke prevention in atrial fibrillation patients utilize a rigid, cylindrical support frame with tissue-piercing fixation members and macroporous filtering membranes that allow the passage of blood. These devices have a number of issues and/or potential drawbacks. The opening (ostium) of the left atrial appendage varies in geometry and size. Sealing the left atrial appendage with a rigid frame that presupposes a circular ostium can be less effective at preventing thromboemboli from entering systemic circulation.

Securing a device in the left atrial appendage is a major safety concern to physicians. Many of the current left atrial appendage occlusion or filtering devices employ tissue-piercing fixation members. The tissue of the left atrial appendage is generally fragile and thin. The heart is encased in a tough, non-elastic pericardial sac. This makes bleeding from the heart through the holes caused by the tissue-piercing fixation members into the pericardial space a potentially life-threatening situation due to the potential for tamponade (compression of the heart when blood or fluid builds up in the space between the myocardium (heart muscle) and the pericardium (outer covering sac of the heart)).

Another concern with many of the current devices is the filtering type membranes. These membranes are macroporous and do not provide immediate cessation of blood flow through the membrane. Such membranes can take hours to weeks to substantially occlude. The possibility exists for thromboemboli to enter the blood stream while the clotting/occluding process of the filtering membrane takes place. Many of these atrial fibrillation patients are on some type of blood thinning (anticoagulant or antiplatelet) medication, which could prolong the clotting/occluding process for these filtering membranes and expose patients to stroke risk.

SUMMARY OF THE INVENTION

Occlusive devices have been discovered comprising a membrane component configured to inhibit passage of blood and an expandable frame formed from a plurality of wires having a cupped occlusive component at least partially covered with the membrane component, one or more anchors with looped ends and a hub component.

Some embodiments of an occlusive device of the present invention comprise a membrane component configured to inhibit passage of blood; and an expandable frame having a distal end and a proximal end and having: a cupped occlusive component, one or more anchors, and a hub component between said occlusive component and said one or more anchors. In some embodiments the cupped occlusive component is at least partially covered by said membrane component. In some embodiments one or more of the anchors has a looped end. In some embodiments the expandable frame is formed from a plurality of wires extending from a proximal end to a distal end of said frame.

Some embodiments comprise an occlusive device comprising a proximal portion, having a membrane component configured to inhibit passage of blood and an expandable frame formed from a plurality of wires having a cupped occlusive component at least partially covered with the membrane component, connected by at least one flexible connector to a distal portion having one or more anchors.

Some embodiments comprise a membrane component configured to inhibit passage of blood; and an expandable frame having a distal end and a proximal end and having: a cupped occlusive component having a first configuration upon application of tensile force and a second configuration upon release of said tensile force, one or more anchors, and a hub component between said occlusive component and said one or more anchors. In some embodiments the cupped occlusive component is at least partially covered by said membrane component. In some embodiments the configuration of the cupped occlusive component is a tube. In some embodiments the second configuration is a cupped shape formed from at least two overlapping petals configured to allow movement between the at least two overlapping petals. In some embodiments the expandable frame is formed from a plurality of wires extending from a proximal end to a distal end of said frame.

Other advantages, benefits and novel features of the embodiments of the present invention will become apparent from the following detailed description and accompanying drawings. All references, publications and patents, including the figures and drawings included therewith, are incorporated by reference in their entirety.

BRIEF DESCRIPTION OF THE DRAWINGS

FIG. 7 illustrates a device placed on a delivery catheter situated in a delivery sheath.
FIG. 8 illustrates an alternate method of placing a device on a delivery catheter situated in a delivery sheath.
FIGS. 15A-D illustrate a flexible wire connector.
FIGS. 17A-B show a flex joint with a chain link type of connection.
FIGS. 20A-H show various types of flexible connectors.
FIGS. 22A-C show various configurations of a flexible connector.
FIG. 23 illustrates an embodiment of an anchor.

DETAILED DESCRIPTION OF THE INVENTION

Despite various efforts in the field, there remains an unmet need for minimally invasive methods and associated devices for cardiovascular occlusion, particularly in the left atrial appendage. The devices of the present invention conform to the anatomy of a variety of left atrial appendage ostia, demonstrate firm and secure anchoring with reduced risk of trauma and bleeding from anchoring, and provide rapid cessation of blood flow across the occluding membrane.

The invention relates to occlusive devices useful in occluding holes, defects, or appendages in the body of a patient, including the heart, such as right or left atrial appendages, fistulas, aneurysms, and patent ductus arteriousus, and methods of making and using the same. The occlusive devices provide a frame that is compliant enough to conform to a wide variety of opening geometries and sizes. Particularly, embodiments of the devices can provide a left atrial appendage occlusion device frame that provides firm, secure anchoring with significantly reduced clinical sequela from piercing or without traumatic piercing of the left atrial appendage tissue. Some embodiments provide a membrane component configured to inhibit the passage of blood through the membrane, i.e., substantially occludes the flow of blood through the membrane. Some embodiments provide a membrane that is configured to induce rapid tissue ingrowth and immediately occludes the passage of blood through the membrane.

Although atrial fibrillation can result in blood clots originating in the left atrial appendage and the occlusive devices will be illustrated herein with regard to use with the left atrial appendage, the devices of the present invention can also be used on the right atrial appendage and, in general, for placement across any aperture of the body, including in the vasculature, where there is a need to prevent blood clots from escaping or to inhibit or substantially reduce blood flow.

Some embodiments provide a membrane component configured to inhibit passage of blood and an expandable frame formed from a plurality of wires having a cupped occlusive component at least partially covered with the membrane component, one or more anchors with looped ends, and a hub component. Each of the one or more anchors may have one more or looped ends, and may further include one or more passive barbs.

In some embodiments, anchors with looped ends are single-leg anchors. In some embodiments, anchors with looped ends include a first leg and a second leg, each leg converging at the second end of each leg to form a loop.

Figure 1:
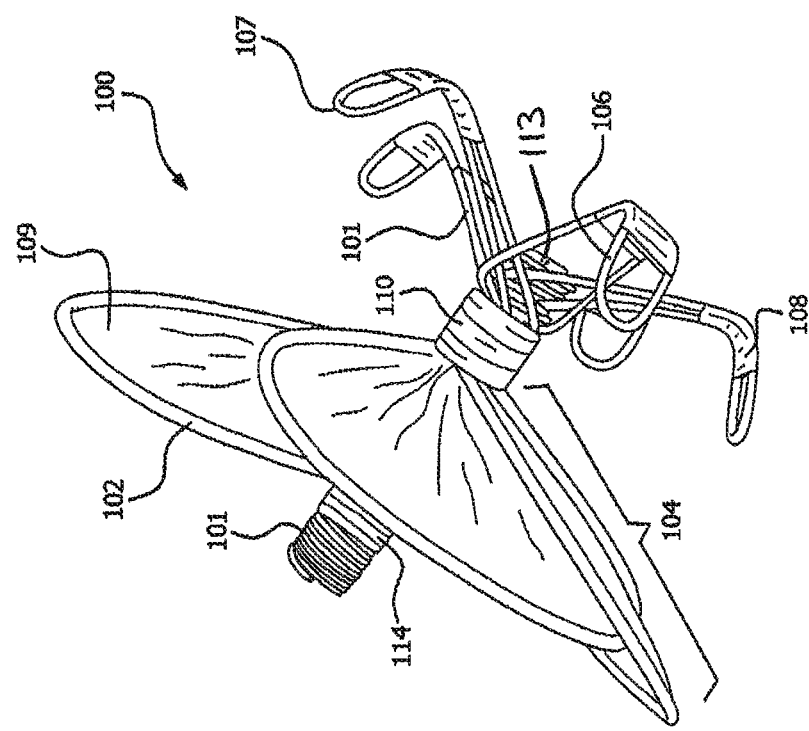
FIG. 1 is a perspective view of an embodiment of the device.
Figure 2:
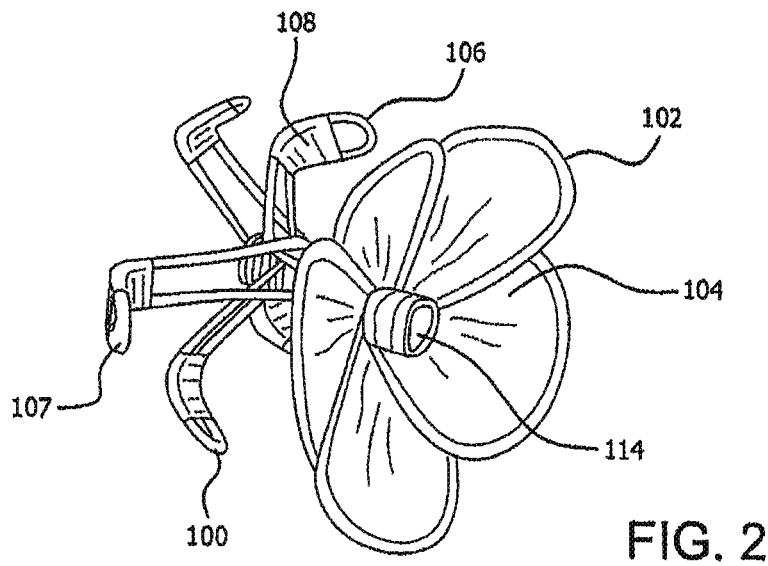
FIG. 2 provides a perspective view of the device of FIG. 1.
Figure 3:
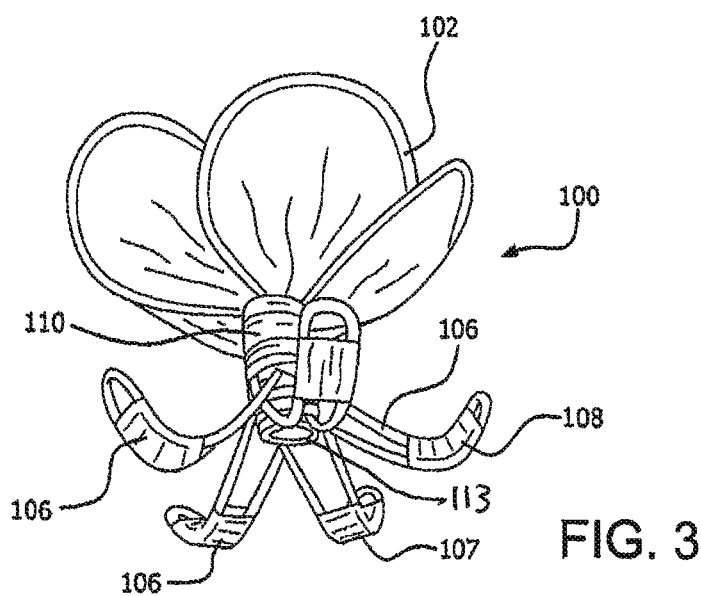
FIG. 3 provides an alternate view of the device of FIG. 1.
Figure 4:
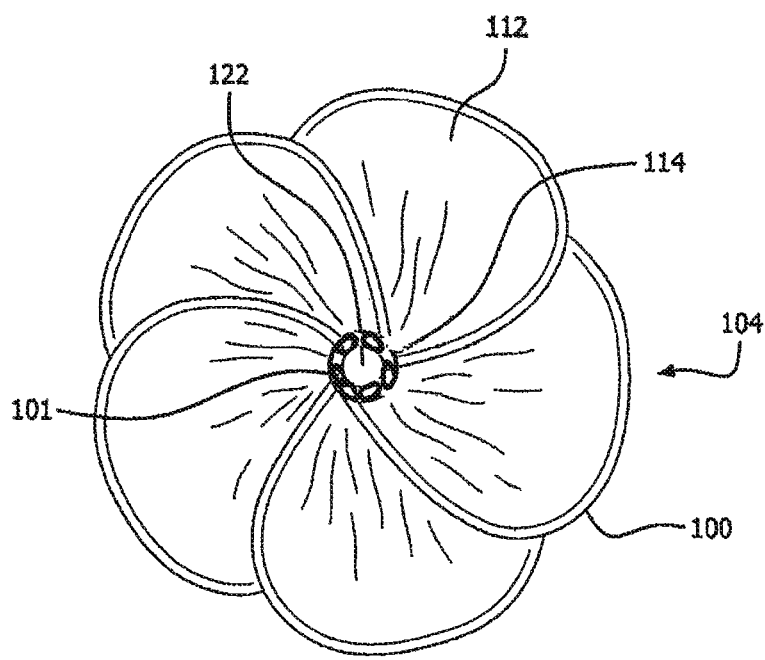
FIG. 4 provides an end on view of the device of FIG. 1.

FIGS. 1 to 3 are prospective views from three different angles looking at the device 100 shown in its fully deployed state without any diametrical constraint (such as it would have when contained within a delivery catheter or, to a lesser extent as it would have within an atrial appendage). FIG. 4 is an end view of device 100 looking into the cupped, concave side of the proximal end of device 100.

Device 100 can be manufactured from multiple individual lengths of flexible, fatigue resistant wire 101 as will be further described. In some embodiments, the proximal end of device 100 can have a proximal eyelet 114, and a distal eyelet 113 located adjacent the distal end of device 100. A lumen can extend through both eyelets 113 and 114 and through the length of device 100. Device 100 also can have an occlusive component 104 located adjacent the proximal end and one or more anchors 106 located at the opposing distal end, with the occlusive component 104 and one or more anchors 106 separated by hub 110. The occlusive component 104 can comprise multiple petals 112, each petal 112 having an expandable frame 102 formed from a portion of a length of wire 101. Each petal 112 can be covered or substantially covered with a membrane component 109 that is supported by expandable frame 102. In some embodiments, a single membrane covering 109 can be used to substantially cover all multiple petals 112.

In some embodiments one or more anchors 106 and/or barbs 211 contact the wall or body of the left atrial appendage. In some embodiments the point of contact between the anchors and/or barbs is the endocardial surface within the left atrial appendage. While in some embodiments one or more anchors and/or barbs penetrate into the endocardial surface of the left atrial appendage, in some other embodiments, there is no penetration of the endocardial surface. In some embodiments, some anchors of the device penetrate the endocardial surface while other anchors of the device do not penetrate the endocardial surface. In some embodiments, some barbs of the device penetrate the endocardial surface while other barbs of the device do not penetrate the endocardial surface. In some embodiments one or more anchors contact trabeculation of the endocardial surface.

In some embodiments, one or more anchors 106 are formed from portions of the lengths of wires 101. In some embodiments, two or more, three or more, four or more, five or more, six or more, seven or more, eight or more, or nine or more anchors stabilize and/or secure the device 100. Further examples of anchors are provided below.

In some embodiments, one or more anchors 106 has a looped end 107 and is provided with a membrane covering 108 over a portion of the individual anchors 106. FIGS. 1 to 4 show an embodiment of an occlusive device 100. In some embodiments of the device 100, the device is constructed with an expandable frame 102. The expandable frame comprises the proximal eyelet 114 and a distal eyelet 113, the cupped occlusive component, one or more anchors, and a hub component located between the occlusive component and said one or more anchors. The expandable frame 102 can be formed in any size appropriate for an application. Typically the size of a human left atrial appendage ostium ranges from about 10 to about 32 mm with the average being about 21 mm plus or minus about 4 mm. Device sizes can be manufactured to encompass the entire range of ostium sizes. Expandable frame 102 can be constructed from any number of fatigue resistant wires 101. In some embodiments multiple wires, e.g. four, five, six, seven, eight, nine, or more wires are used in the manufacture of the device. The expandable frame 102 is constructed from wires, for example fatigue resistant wires, that have elastic properties. In some embodiments expandable frame 102 is constructed of wires that have elastic properties that allow for expandable frame 102 to be collapsed for catheter-based delivery or thoracoscopic delivery, and then self-expand to the desired configuration once positioned in a cavity. The elastic wire can be a spring wire, a shape memory alloy wire or a super-elastic alloy wire. Any wire can be used that has biocompatible characteristics and is strong, flexible, and resilient. The wire can be, for example, nitinol (NiTi), L605 steel, stainless steel, or any other biocompatible wire. The elastic wire can also be of a drawn-filled type of nitinol containing a different metal at the core. The super-elastic properties of nitinol make it a useful material for this application. Nitinol wire can be heat set into a desired shape. Stainless steel wire is an alternative material. It can be plastically deformed into a desired shape. Wire that is formed to have varying diameters with a centerless grind technique can also be used. Other shape memory or plastically deformable materials can be suitable in this application.

In some embodiments, expandable frame 102 can be constructed of a drawn-filled type of NiTi wire containing a radiopaque metal such as platinum at the center. Upon deployment, the wire structure resumes its deployed shape without permanent deformation.

Expandable frame 102 and other embodiments of the expandable frames can be formed from elastic wire materials that have outer diameters (OD) between about 0.12 and about 0.4 mm. Other embodiments can be formed from wires with OD of from about 0.2 to about 0.3 mm.

As used herein, the term "about" means a value falling with the range encompassed by +/−5% or +/−10% of given value.

Figure 6:
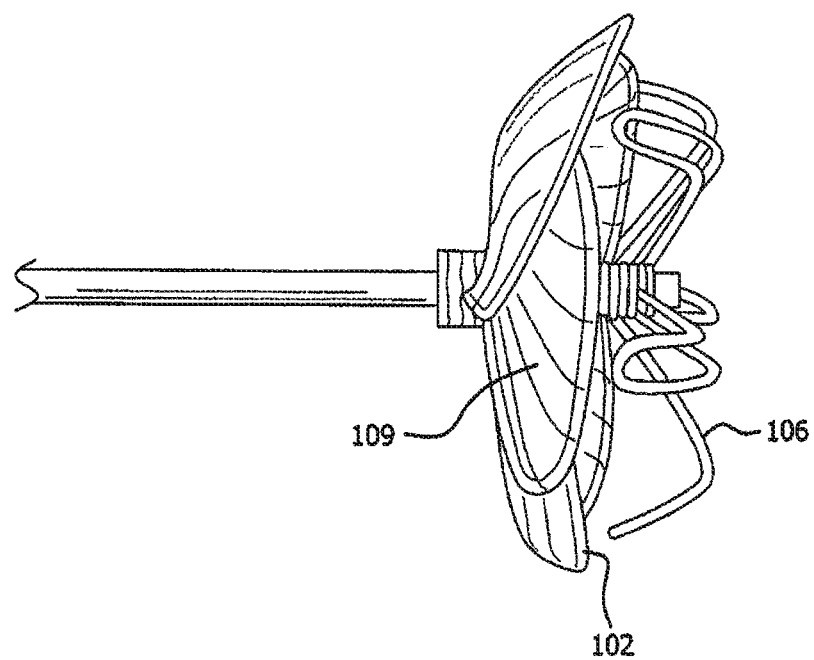
FIG. 6 illustrates an embodiment of the device.

When formed, expandable frame 102 comprises a proximal eyelet 114, a distal eyelet 113, a cupped occlusive component 104, a hub component 110 and anchor elements 106. The cupped occlusive component 104 is designed to effectively seal or occlude the left atrial appendage. "Cupped", as used herein, means the occlusive component 104, as seen when device 100 is deployed without constraint, is non-planar. The cupped shape of the occlusive component 104 is configured to enhance sealing around the edges of the ostium of the left atrial appendage and apposition to the lateral wall of the left atrium of the heart. The cupped occlusive component 104 has a concave or convex configuration that allows versatility in device sizing as well as promotes self-centering of the device in the left atrial appendage ostium. An occlusive component 104 with a concave configuration is shown in FIGS. 1 to 4. An occlusive component 104 with a convex configuration is shown in FIG. 6.

The occlusive component 104 comprises multiple petals 112, i.e. at least two petals, and in some embodiments five petals or more. In some embodiments the multiple petals are present in the occlusive component in odd numbers. The occlusive component 104 comprises multiple petals 112 that are spaced uniformly apart. In some embodiments the multiple petals 112 are spaced uniformly apart, i.e. the apex of each petal 112 is equally spaced about the circumference of the occlusive component 104. In some embodiments, the individual petals move independently from one another within the restraint of the membrane component. Constructing cupped occlusive element 104 of multiple petals 112 increases the conformability of the device to non-circular orifices, which provides for more effective tissue apposition and sealing. The multiple petals 112 also increase the uniformity of the radial force exerted on body tissues, which provides added safety.

The pre-set elastic wire configuration of expandable frame 102 allows the frame to twist during deployment. This twist forms petals 112. Deployed petals 112 form the outer diameter 120 of the expandable frame 102. Deployed petals 112, when covered with membrane component 109, form the cupped occlusive element 104. In some embodiments petals 112 are formed to have overlapping zones to improve sealing qualities. The radius and shape of petals 112 can be optimized to minimize sharp bend angles in the elastic wire and to minimize unsupported sections of petals 112 to improve sealing qualities of the device, reduce bending fatigue in the wire and aid in reducing device loading forces.

In an embodiment as described in Example 1, during the construction of the device, the longest distance between the center pin 22 and the outer surface of the petal jig 38 (illustrated in FIG. 11) establishes the radius of the occlusive component. While in some embodiments there are five petals, however, in some embodiments there are two, three, four, six, seven, or eight or more petals. In some embodiments at least one of the petals is covered with a membrane component 109 to inhibit the passage of blood through the petals. In some embodiments, each of the petals is at least partially covered with a membrane component. In some embodiments each of the petals is fully covered with a membrane component. Proper positioning and seating of the device is facilitated by the cupped occlusive element 104 and inhibits blood flow through or around the device.

Some embodiments of the device are constructed using multiple wires that extend the full length of the device, thereby resulting in a one-piece expandable frame. Alternatively, a multiple-piece embodiment of the device can be constructed by joining a proximal portion to a distal portion at the hub 110, e.g. a two-piece device. In creating a two-piece construction, the proximal portion and the distal portion can be connected in a variety of ways. The proximal portion can comprise an occlusive component, a proximal eyelet and, optionally, a hub. The distal portion can comprise one or more anchors, a distal eyelet, and optionally a hub component. The proximal portion and the distal portion can be joined, for example, with the use of a fluorinated ethylene propylene (FEP) coated expanded polytetrafluoroethylene (ePTFE) film wrapped to join the two parts together and subsequently heated to create a durable bond. In some embodiments, the pieces are joined by a concentric fit, in which one piece is screwed or press fit into the other. In some embodiments two piece construction is utilized wherein each of the pieces is created with different wire types or diameters. For example, in some embodiments the device can be tailored to have an anchor element that is stiffer than the occlusive element. That is, the distal portion can be constructed with a stiffer (e.g., larger diameter) wire than what is used to create the proximal portion.

The proximal portion and distal portion can also be connected with a flexible connector region 124 between the two elements. In such embodiments, a proximal portion has a membrane component configured to inhibit passage of blood and an expandable frame formed from a plurality of wires having a cupped occlusive component 104 at least partially covered with the membrane component, connected by at least one flexible connector and/or a hub to a distal portion having one or more anchors 106. Such connectors can include hinges, springs, and joints.

In some embodiments the flexible connector region 124 is located at or below the hub 110. In some embodiments, the connector component is constructed by winding the wires between the proximal portion and the distal portion into a spring-like configuration. The spring-like configuration can be formed by winding the wires to form an eyelet 142 at the distal portion of the cupped occlusive element 104 and an eyelet 144 at the proximal portion of the anchor component 106 with additional windings 140 in between the two eyelets 142,144 illustrated in FIG. 15A.

Figure 15B:
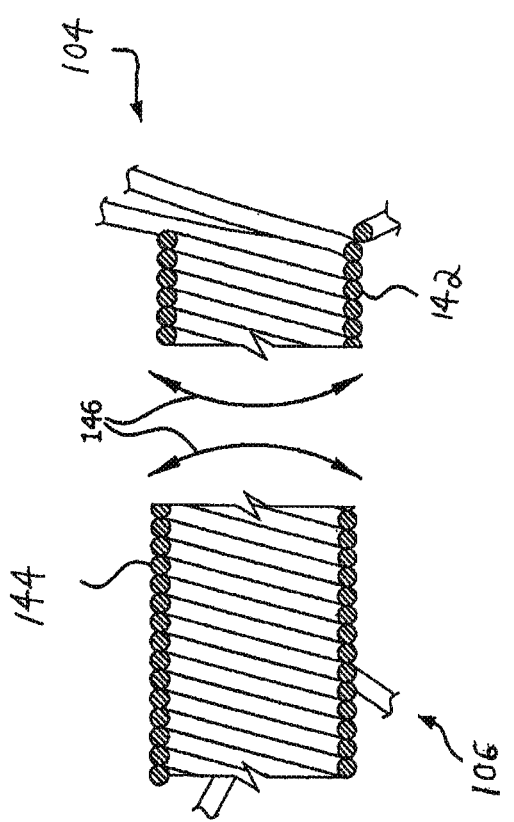
Figure 15C:
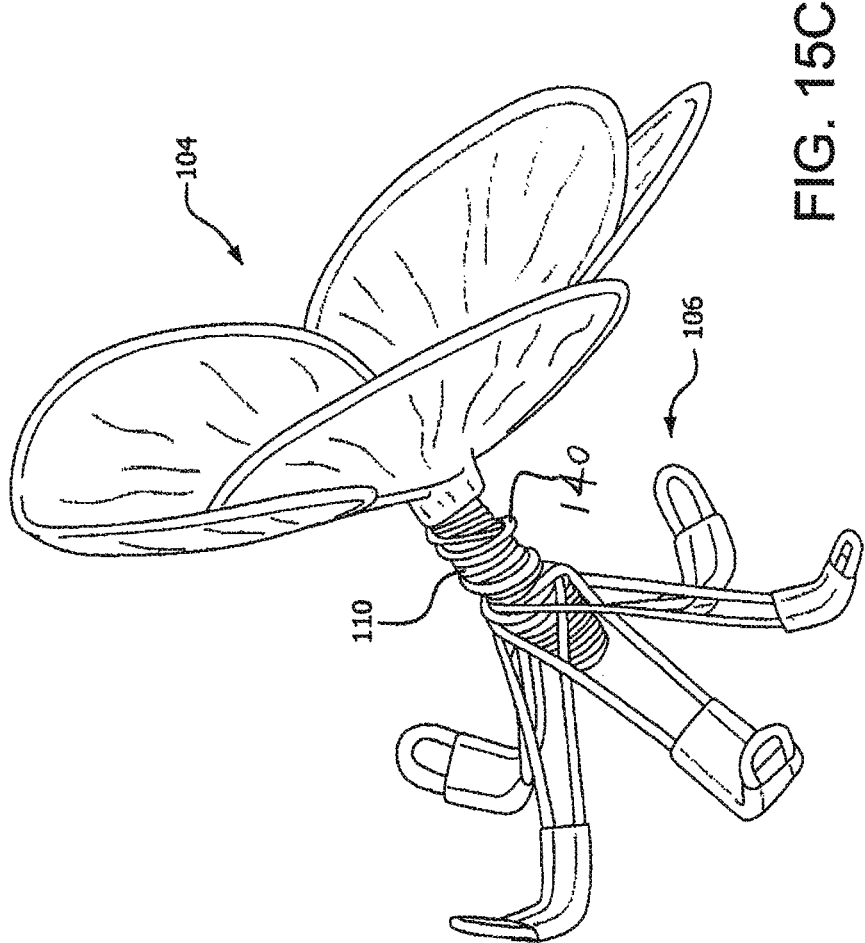

FIG. 15B is a longitudinal cross section that further illustrates a configuration with an eyelet at the distal portion of the cupped occlusive element 142 and an eyelet at the proximal portion of the anchor element 144 separated to show space where flexible connectors can be inserted. Wires of the additional windings 140 can then be cut out to change the performance characteristics of the middle spring-like section. The spring-like center section can also be formed by winding the wires directly from the cupped occlusive element into the anchor component with no eyelets formed. A spring-like connector can be formed separately from the cupped occlusive member and the anchor component and be secured to each by an interference fit either over the eyelet at the distal portion of the cupped occlusive element 142 and the eyelet at the proximal portion of the anchor element 144 or on the inner diameter of the eyelets 142 and 144 as shown in FIGS. 15C and 15D (144 not shown in FIG. 15C). This connection may be enhanced by the addition of a fastener including, for example, glue or adhesive tape.

Figure 16A:
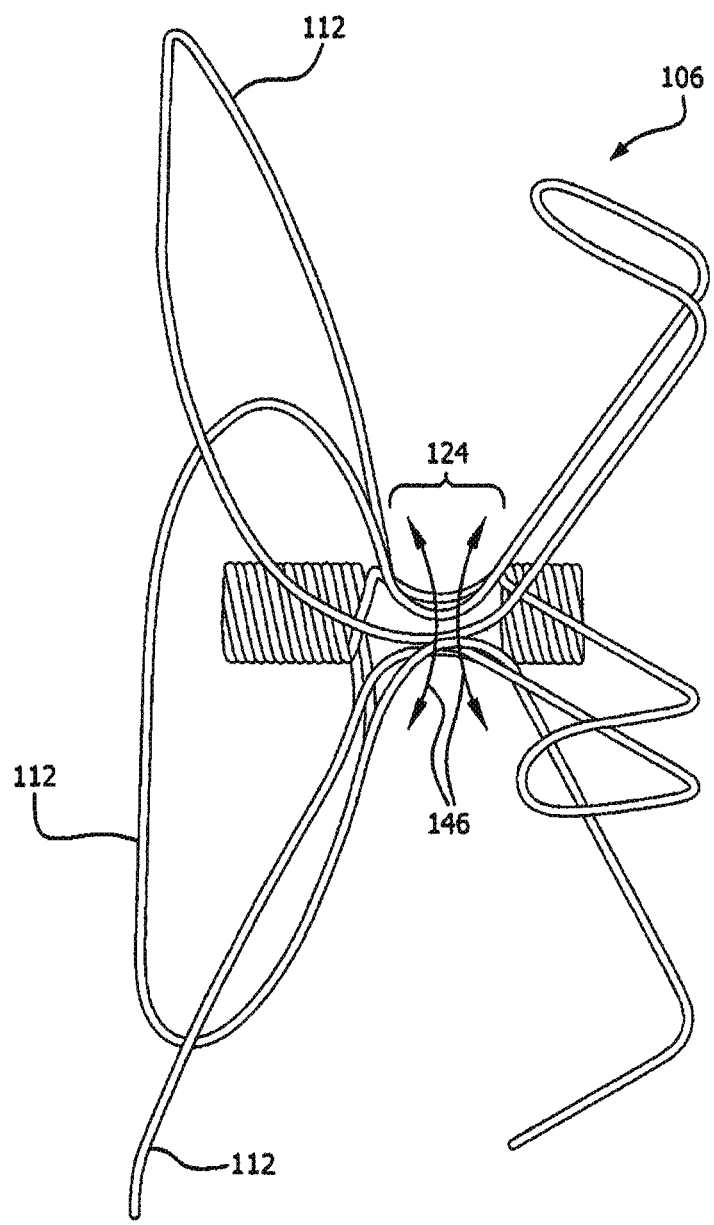
FIGS. 16A-B show a flexible wire connector.
Figure 16B:
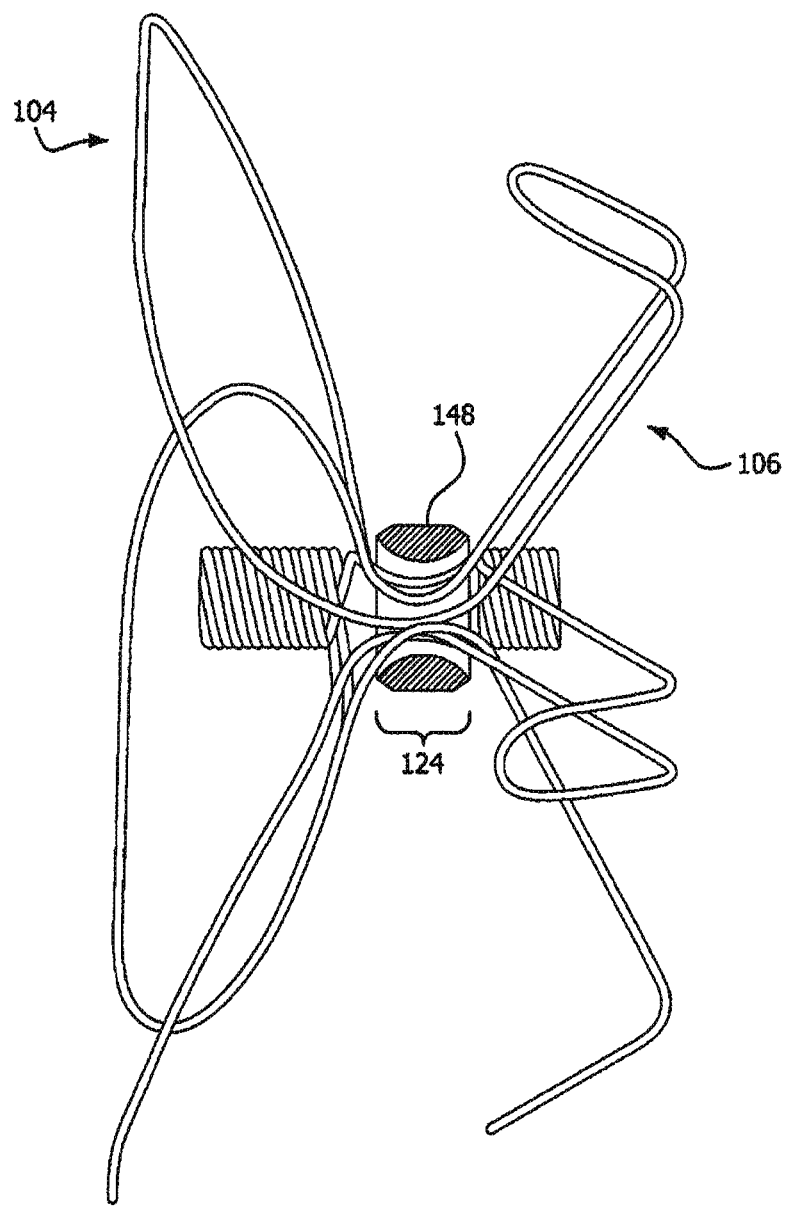

In some embodiments, a flexible wire connector is formed from the wires that form the petals 112 shown in FIG. 16A with articulation arrows 146 indicating that the device can be bent along its longitudinal axis. In this configuration, the flexible wires continue from the petals 112 through the flexible connector region 124 to continue to the anchor components 106. Such a configuration can, in some embodiments, include a constraint or flexible tube 148 loosely fit around the flexible connector region 124, as shown in FIG. 16B. The constraint may be constructed of any suitable materials as described herein for flexible tubes.

Figure 17A:
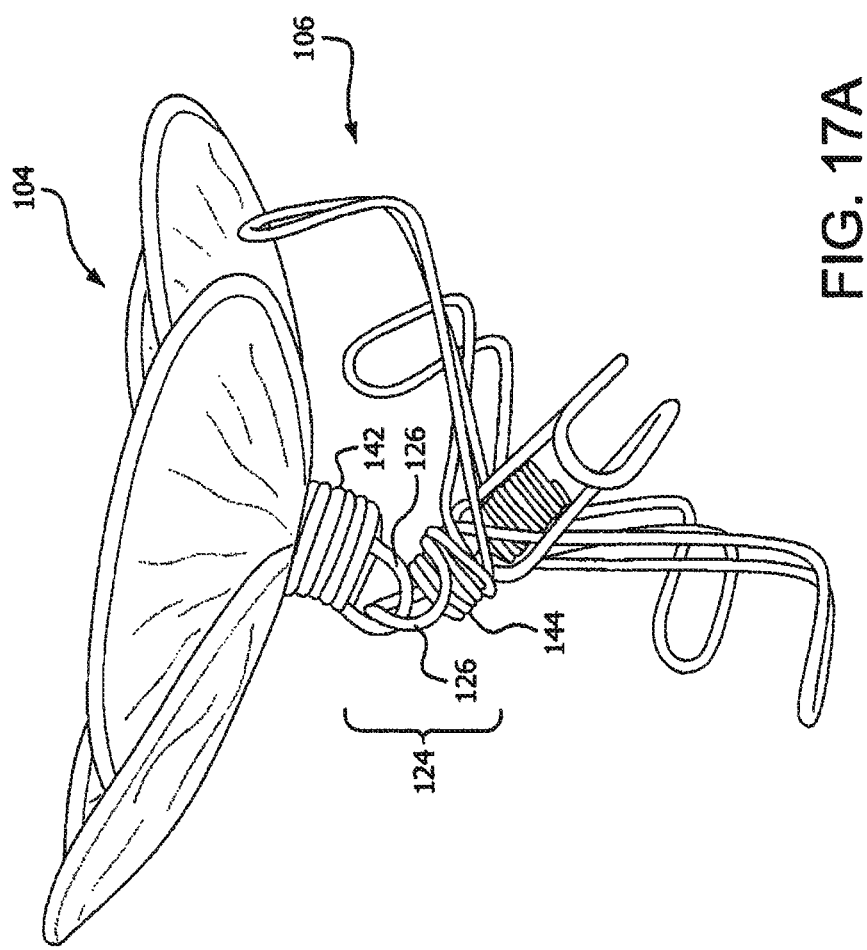

The connector component can, for example be configured of two wire loops 126 that form a connection similar to that of a chain link connection as shown in FIGS. 17A and 17B. Wire loops 126 may be secured within the eyelets, for example, by any appropriate adhesive, by welding or by a mechanical connection. Alternately or additionally, wire loops 126 may be formed of one or more of the wires that form the eyelet. The chain link type of connection may be covered by a flexible sleeve 128 (approximate range of motion is indicated by arrows 127) as shown in FIG. 17B, or left uncovered as shown in FIG. 17A. Materials used for such a sleeve 128 can be any material with the appropriate biocompatibility and fatigue performance characteristics such as those listed below in relation to a flexible tube connector.

Figure 18A:
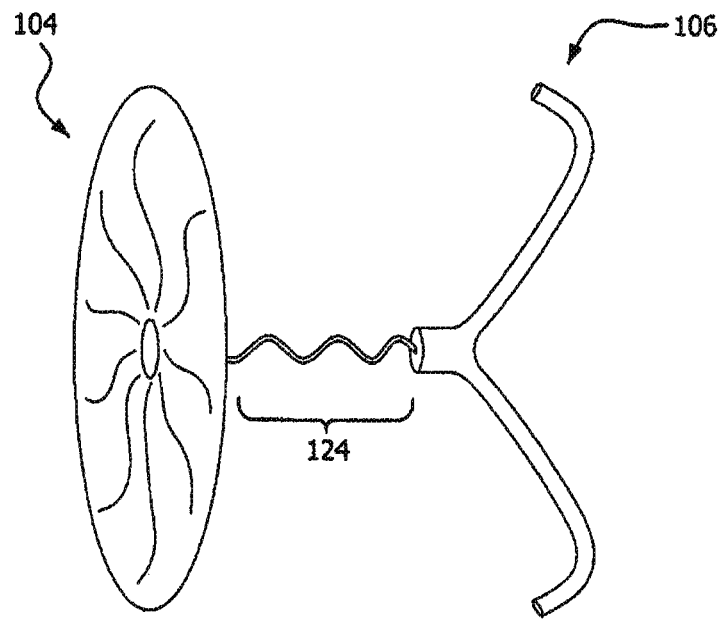
FIGS. 18A-H provide views of types of beaded or flexible connectors.
Figure 18B:
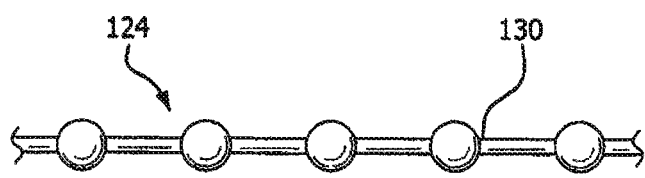

The flexible connector region 124 can be composed of a beaded chain 130 connection. The connector component can be a flexible beaded tube 130 as shown in FIG. 18B. As illustrated in FIGS. 18A-18B, 18D-18G, a beaded chain type of connection can be constructed of flexible beaded chain 130 or fabricated from a nitinol braid 132. In some embodiments the braided chain is a composite of a flexible beaded chain 130 and a nitinol braid 132. The nitinol braid 132 may be heat set into a "bead" type of formation (135, 136) by inserting into the interior of the braid any number of spaced apart ball bearings or other manufacturing aid and then heat treating the structure. The resulting form simulates that of a beaded chain 132 but would, under tension, have a smaller uniform outer diameter due to the extension or elongation of the bead form. The beads resulting from such a treatment can be made of varying sizes 136 as shown in FIGS. 18F-18G.

Figure 18C:
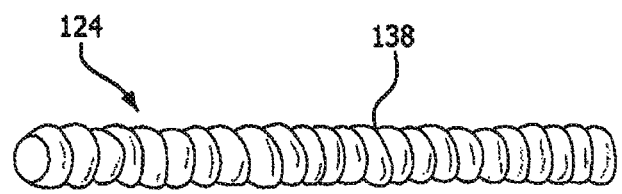
Figure 18D:
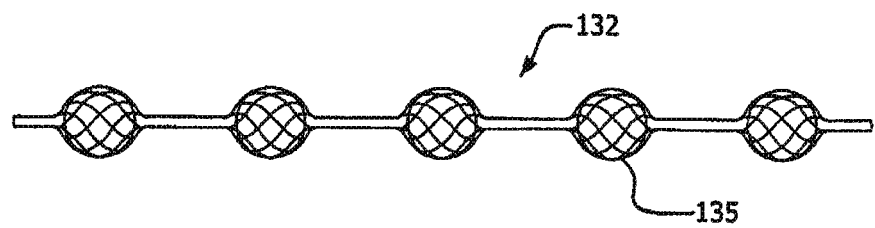
Figure 18E:
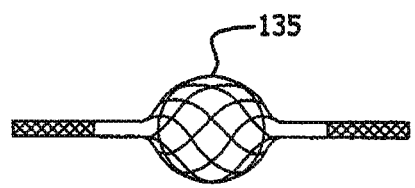
Figure 18F:
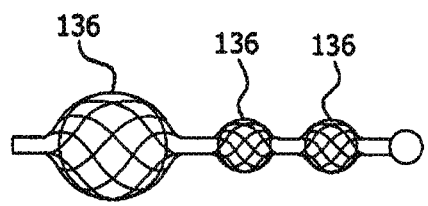
Figure 18G:
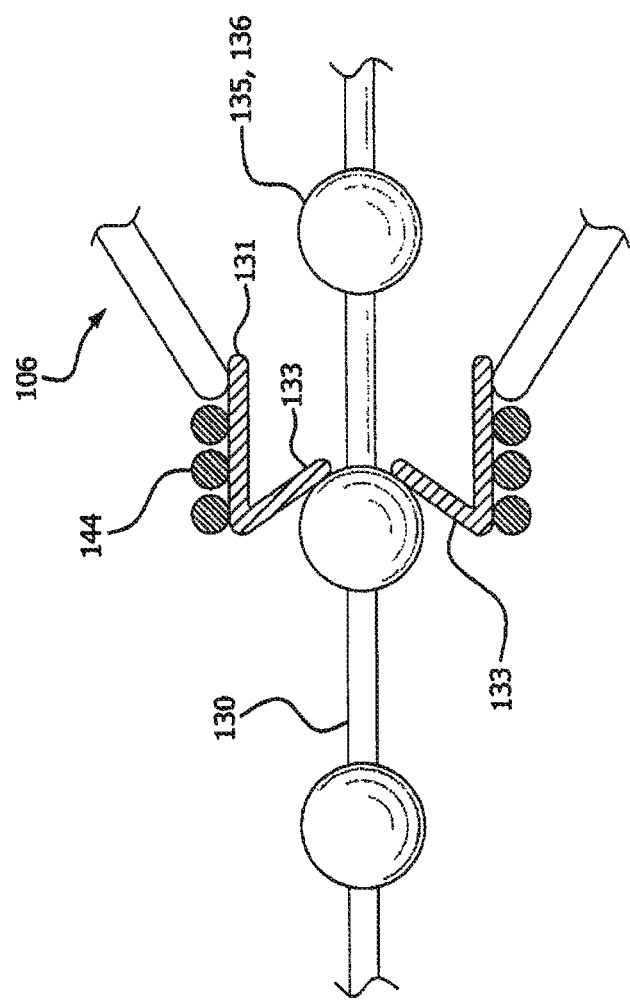
Figure 18H:
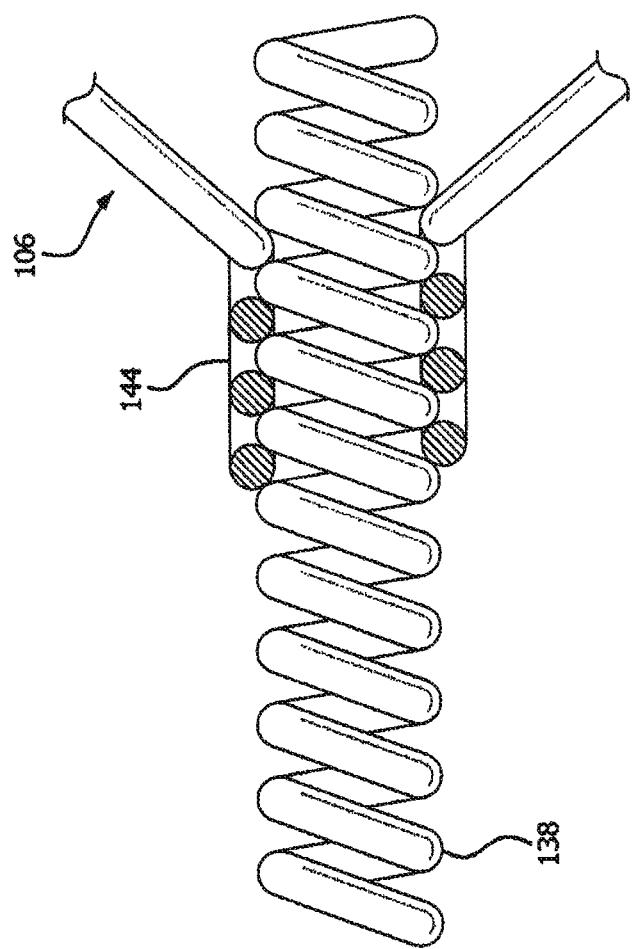

A coil type of flexible connector 138 as shown in FIG. 18C and FIG. 18H may be used as a flexible connector. Such a connector could be formed from any suitable material. In some embodiments such a connector is formed of nitinol wire similar to that used to form cupped occlusive element 104 and anchors 106. A coil type connector 138 can be configured to have a diameter and coil pitch mated to the pitch and diameter of the eyelet at the distal portion of the cupped occlusive element 142 and the eyelet at the proximal portion of the anchor element 144 for securing it within or on both eyelets 142 and 144. Such a connector 138 could be used as described below to provide tactile feedback and length adjustments as shown in FIG. 18H.

In some embodiments the flexible connector is comprised of wires wound into a tubular, spring-like configuration. Some embodiments include the use of 2 or more, 4 or more, 6 or more, or 8 or more filars. In some embodiments the filar wires used have an outer diameter of between 0.1 mm to about 0.3 mm. In some embodiments, the flexible connector is made from flat wire. In some embodiments, the flexible connector is a multi-layer construct including, for example, an inner and outer diameter layer of flat wire running in opposite pitch directions. In some embodiments the flexible connector is a construct including flat wire with braiding.

The flexible connectors shown in FIGS. 18A-18H may also be used to change the length between the eyelet at the distal portion of the cupped occlusive element 142 and the eyelet at the proximal portion of the anchor element 144. In some embodiments the beaded type of flexible chain connectors (135, 136) are set at defined and known lengths from each other which could provide tactile feedback while adjusting the length of the middle of the device. Such a system is shown in FIG. 18G and includes a section of hypotube 131 or other suitably flexible material inserted into the inner diameter of one of the eyelets 142 and/or 144 configured to have inner protrusions 133 to provide tactile feedback during length adjustment. In some embodiments, the device is configured so as to permit rotational flexibility and/or length adjustability. For example, some embodiments of a device as shown in FIG. 18G allows length adjustability as discrete beads on 130 pass thru a deformable gate 133 as a result of maneuvers performed by the implanting clinician. In some embodiments length can also be adjusted using a screw type mechanism where the coils of 138 pass thru the threads on 144. In some embodiments, a flexible connector permits both rotational flexibility as well as length adjustability.

Figure 19A:
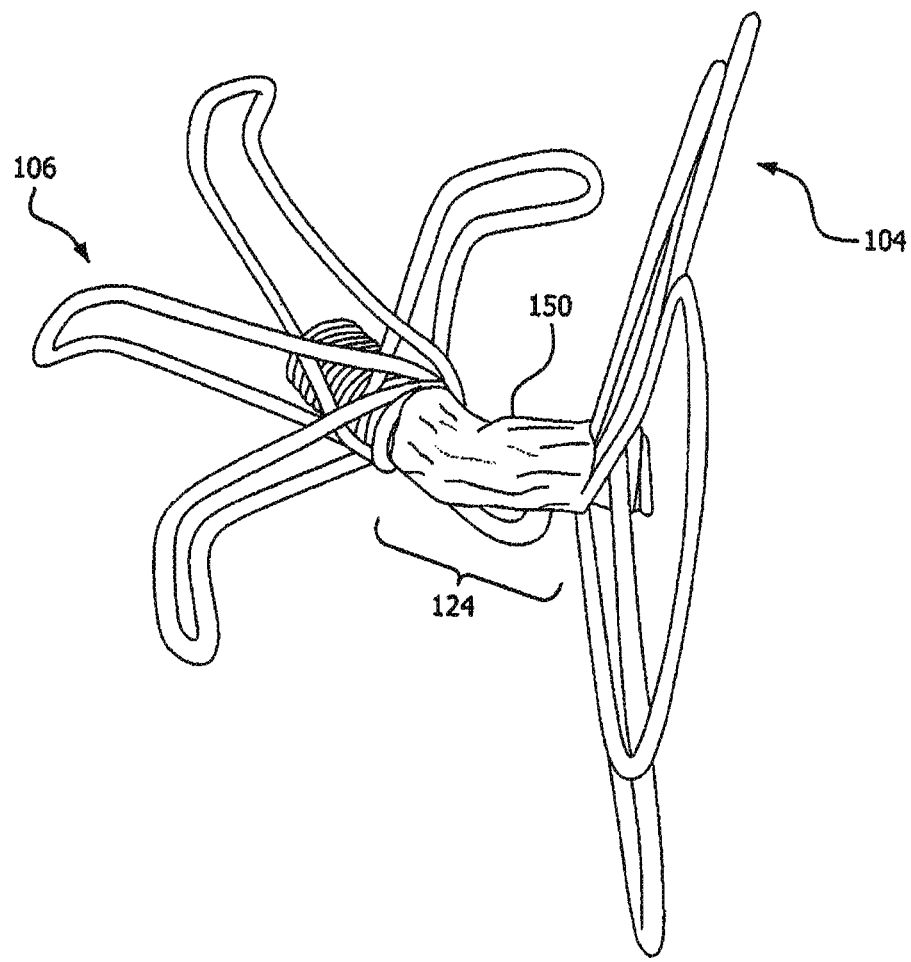
FIGS. 19A-B show an ePTFE tube flexible connector.
Figure 19B:
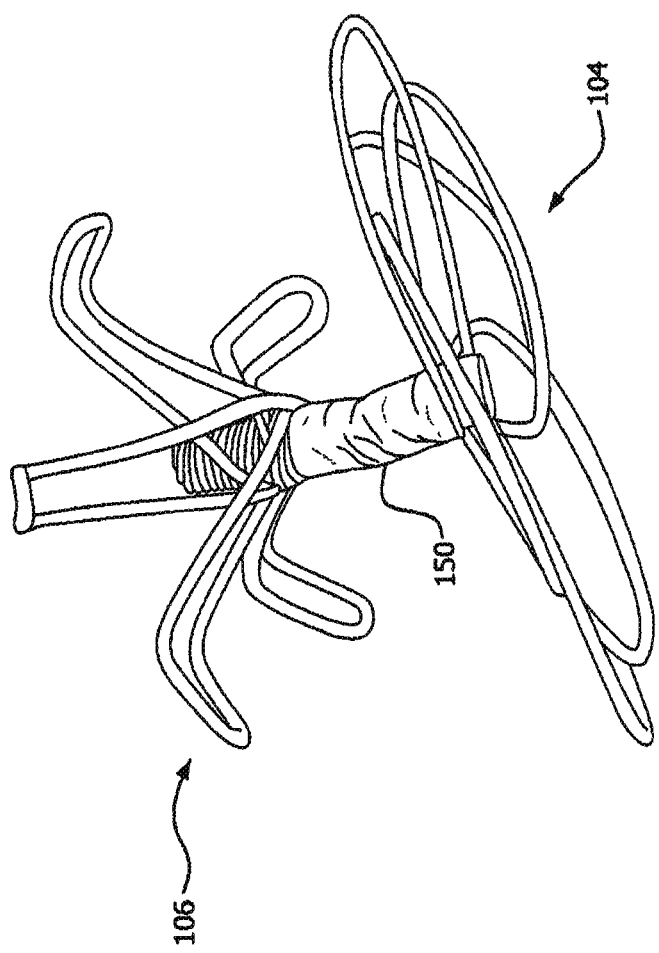
Figure 20A:
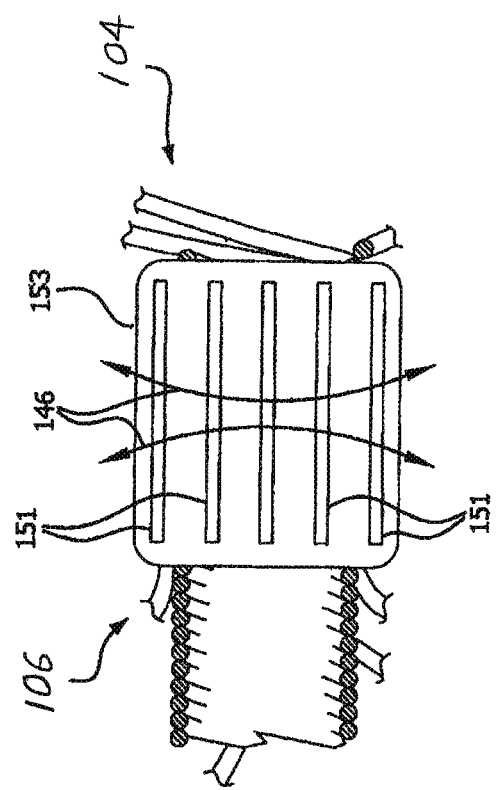
Figure 20B:
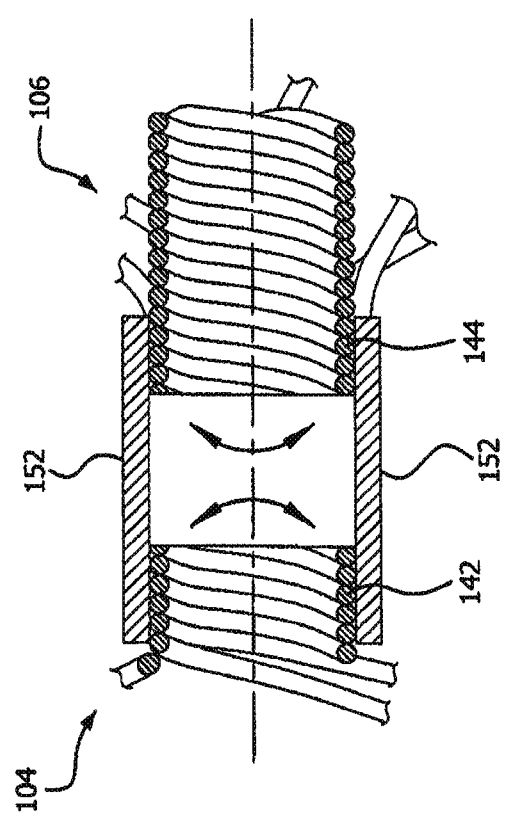
Figure 20C:
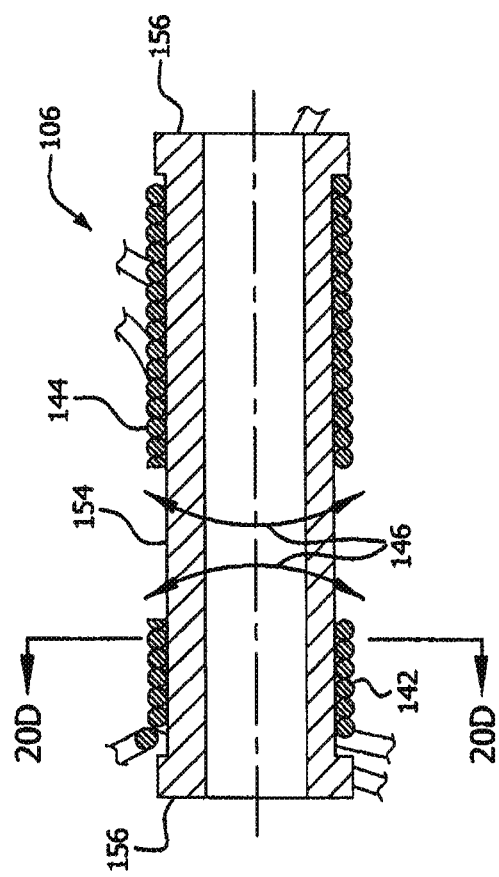
Figure 20D:
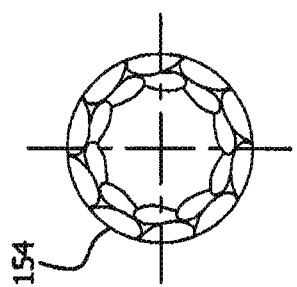

The flexible tube can be any suitable polymer. In some embodiments the tube is ePTFE. As shown in FIGS. 19A-19B such a flexible tube made from ePTFE 150 can be connected over the eyelet at the distal portion of the cupped occlusive element 142 and the eyelet at the proximal portion of the anchor element 144 (not shown) and secured using various means as described herein. In some embodiments the ePTFE tube has one or more densified portions. The tube can be a knitted polymer tube, strand or stranded rope. A tube may also be formed from shrink tubing 152 such as, but not limited to, extruded PTFE, reinforced silicone 153 (FIG. 20A) or helically wrapped PTFE film as illustrated in the longitudinal cross section FIG. 20B. Reinforcing member 151 can be constructed of any biocompatible metal such as L605, SST, 316L and the like. The shrink tubing 152 may be adhered to eyelets 142 and 144 by an interference or pressure fit or with any appropriate adhesive. The tube may have bellows similar to those in a bending straw. The bellows can be incorporated into either a metal tube or a polymer tube. The metal tube 154 can be a helically wound hollow tube with one or more layers of helically wound filaments as shown in FIG. 20C-20D. The metal tube 154 can also be a cut hypotube in a variety of patterns shown in FIG. 15E. Such tubes may be configured to have a flange 156 at one or both ends to facilitate attachment to the eyelets 142 and 144 of the cupped occlusive member and the anchor components.

In some embodiments, the flexible connector protrudes through eyelets of the occluding disc and the anchoring structure. In some embodiments the flexible connector include caps mounted to the ends of the hypotube. In some embodiments the caps are welded, permanently affixed (e.g., superglue, FEP) to the flexible connector. In some embodiments the end caps prevent movement of device components (i.e. petal supports and anchors) past their respective device end points but allow both movement along the longitudinal axis of device as well as rotation about the longitudinal axis of the device. In some embodiments, the flexible connector includes internal spacers to prevent components of the distal end of the device from interfering with, rubbing against, or contacting components of the proximal end of the device. In some embodiments, the internal spacers are a physical spacer or an abraded surface to limit the extent of movement of components along the device's longitudinal axis.

In some embodiments, the flexible connector is a hypotube. In some embodiments, the hypotube has an outer diameter from about 0.06" to about 0.08". In some embodiments the hypotube has a wall thickness of from about 0.1 mm to about 0.2 mm. In some embodiments the hypotube can withstand a tensile load of 2.2 lbs (10N).

Figure 20E:
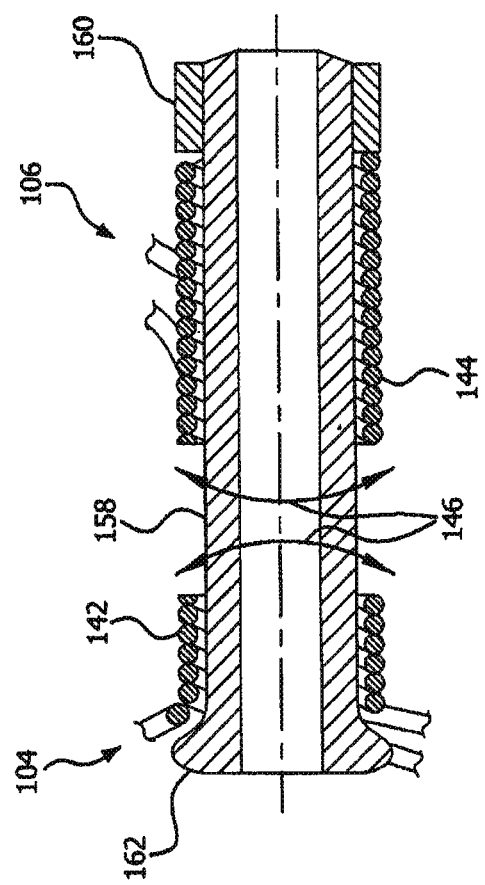

In some embodiments flexible connector 158 is formed of a flexible material such as silicone or urethane as shown in FIG. 20E. This connector can have a clearance fit such that it may be inserted through the eyelet at the distal portion of the cupped occlusive element 142 and the eyelet at the proximal portion of the anchor element 144. It can be secured in place by either use of a formed flange 162 or an attachment cap 160. In some embodiments the configuration allows rotation of one or both of the anchor components or the cupped occlusive element independent of each other. Silicone can also be used to form an over-mold type of flexible connector 164, as shown in FIG. 20G. Attachment of such a connector at eyelets 142 and 144 may be via a typical over molding process, for example.

Figure 20F:
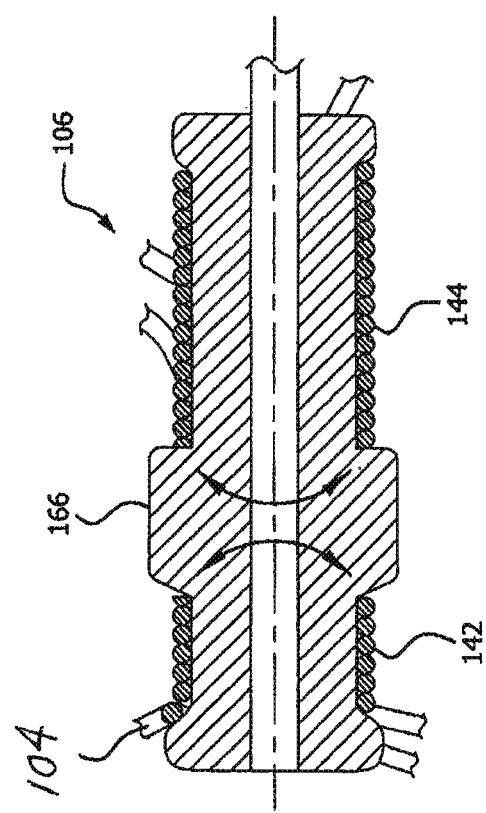
Figure 20G:
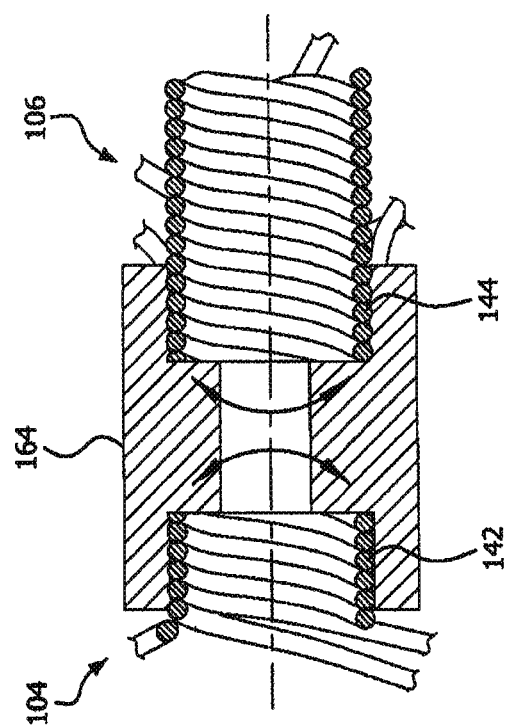

An alternate configuration 166 is shown in FIG. 20F. A silicone or urethane molded insert can be inserted and attached in a similar manner to that described previously. Such an insert may have an increased diameter at the flexible joint.

The flexible connector element can also be a universal joint such as the ball and socket configuration shown in FIG. 20H. The female socket component 168 may be secured or attached within the eyelet at the distal portion of the cupped occlusive element 142 by any suitable means described herein. The ball and shaft 170 are fitted within the female socket component 168 and the entire universal joint covered by a flexible sleeve 172. The flexible sleeve 172 can be any flexible sleeve described herein.

Figure 21A:
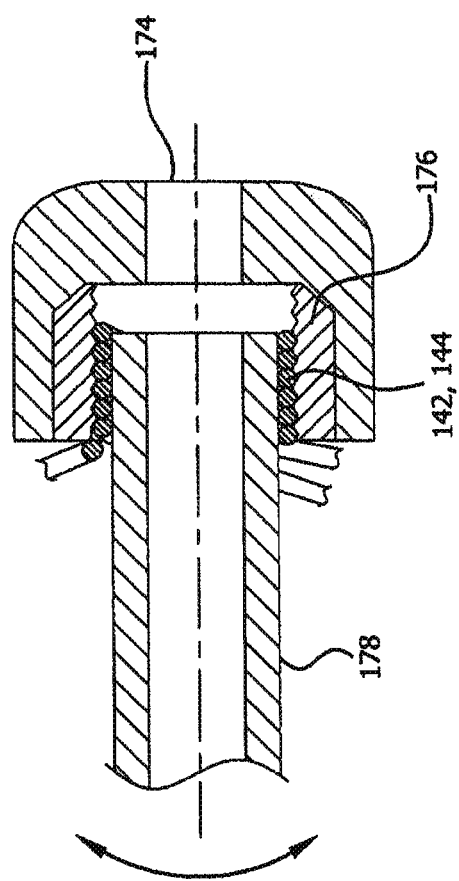
FIGS. 21A-B show various configurations of threaded cap type of flexible connector attachment mechanisms.
Figure 21B:
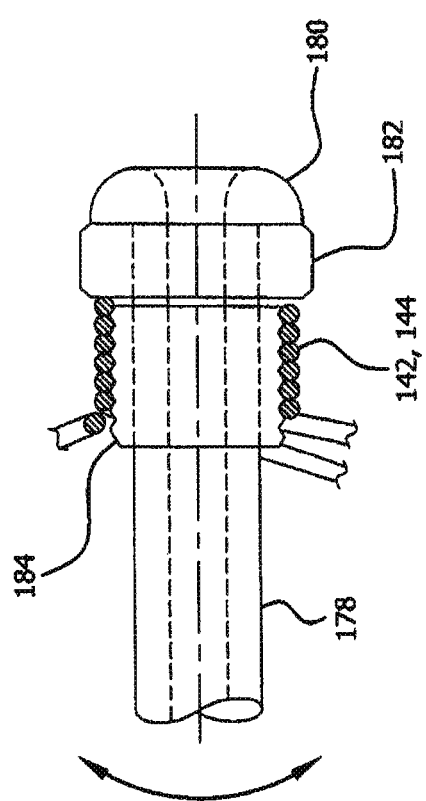

In some embodiments one or more of the flexible connectors can be fixed or attached to eyelets 142 or 144 or both by the use of threaded caps 174 and 180 (shown in FIGS. 21A and 21B). One or more of the threaded caps may be affixed to the flexible tube 178 using a threaded insert 176 having, for example, a multi-thread geometry with a matched pitch coil to that of eyelets 142 and 144. Such a configuration can be used for catheter attachment or device locating or keying. Threaded cap 180 is configured similarly to that of threaded cap 174. The threaded insert 184 is placed on the inner diameter of eyelets 142 or 144 and a flange 182 is used to secure threaded cap 180 to eyelets 142 and 144.

Figure 22A:
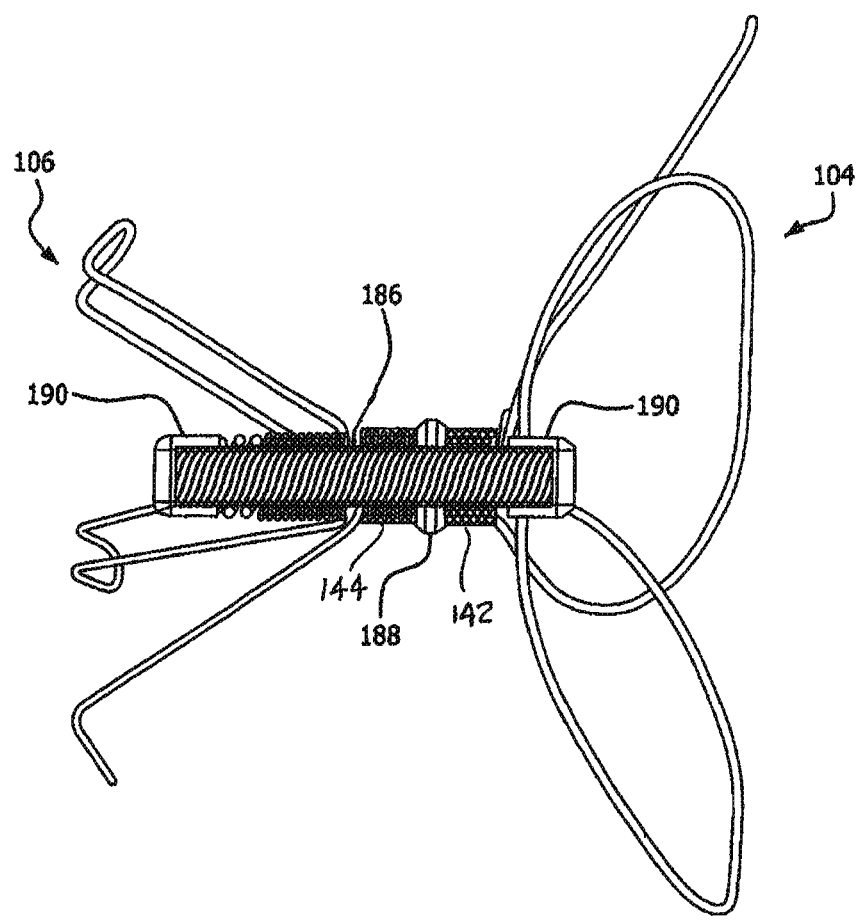

In some embodiments a flexible connector is constructed from a compressed spring. As shown in FIG. 22A, a compressed spring 186 can be constructed with a clearance fit to allow the spring to be inserted through the inner diameter of the eyelets of the device. FIG. 22A depicts a connector portion shown in cross section to provide clarity. The spring construction can be with a wire or filar diameter and wire or filar count to achieve the desired flexibility. In this example, the coil is retained in place with retaining caps 190, which may, in some embodiments, be adhered to the compressed spring with adhesive or with a screw-type fit. Element 188 is a flexible coupling that can be constructed of shrink tubing, PTFE film construct, silicone or any other suitable material. Such a coupling can be constructed with a bellows as described previously. If made from silicone, the flexible coupling 188 can optionally be reinforced with metal, such as a wire or stranded wire construct. Such wire or reinforcing could be constructed of any biocompatible metal such as L605, SST, 316L and the like.

Figure 22B:
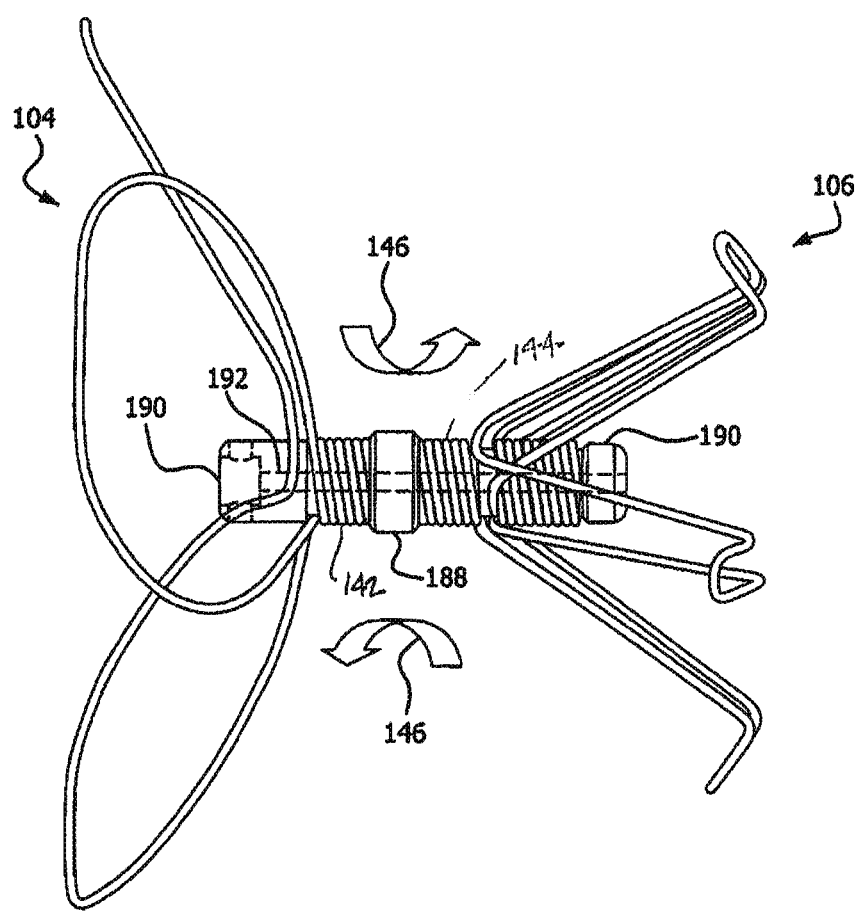

As shown in FIGS. 22B and 22C, an alternative configuration to that of the compressed spring described above can have a cord or filament 192 in the place of the compressed spring 186. End caps 190 can be formed with holes to allow the passage and securing of filament 192. Alternatively, as illustrated in FIG. 22C, cord or filament 192 can be threaded through the lumens of eyelets 142, 144 and secured, such as by knot 194.

The devices 100 can be delivered in an endovascular fashion through a catheter system comprising a delivery catheter 115 located concentrically within a delivery sheath 117. The device 100 can be loaded into a delivery sheath by several methods. One method is to load the device 100 on a delivery catheter 115 and to pull anchors 106 straight and collapse cupped occlusive component 104 in the opposite direction as the anchors, then insert the device and the delivery catheter 115 into the delivery sheath 117 as shown in FIG. 7. Another method is to load the device 100 on a delivery catheter 115, collapse the cupped occlusive component 104 and to collapse or crush the anchors 106 in the same direction as the cupped occlusive element 104, then load the device 100 on the delivery catheter 115 into a delivery sheath 117. Another method of delivery is to extend the cupped occlusive component 104 along the delivery catheter 115 and fold or crush the anchors 106 as described previously, then load the device 100 on the delivery catheter 115 into the delivery sheath 117 as shown in FIG. 8. In some embodiments, the device is delivered over guidewire 119 using rapid exchange or other methods of over the guidewire delivery known to those of ordinary skill in the art (see, for example, U.S. Pat. Nos. 5,040,548, 5,061,273 and 6,165,197 to Yock and U.S. Pat. No. 4,762,129 to Bonzel). In some embodiments, when situated for delivery, the anchors of the device 100 are positioned toward the distal end of the delivery catheter 115 and both device and delivery catheter 115 are positioned within the delivery sheath 117 at the distal end of the sheath 117.

In some embodiments deployment of the devices can be achieved by pushing the devices and the delivery catheter 115 out of the delivery sheath 117, which is held in a constant location. In some embodiments, delivery can be achieved by retracting the delivery sheath 117 while maintaining the location of the device loaded on the delivery catheter 115. In some embodiments a combination of delivery catheter 115 push-out of the anchors 106 accompanied by delivery sheath 117 pull-back for cupped occlusive element 104 deployment can be envisioned. In each of these deployment methods, the anchors 106 would deploy first, and then the cupped occlusive element 104 would be deployed and seated within the ostium. Other methods of deployment can be envisioned by those skilled in the art. A keyed mandrel or delivery catheter can be used for delivery. In such a configuration the lumen of the device can be shaped to match the shape of the mandrel or catheter to improve control of device during deployment. The devices can be adapted for use with commercially available pre-shaped, positionable, bendable, or steerable delivery sheaths and/or catheters.

Figure 26:
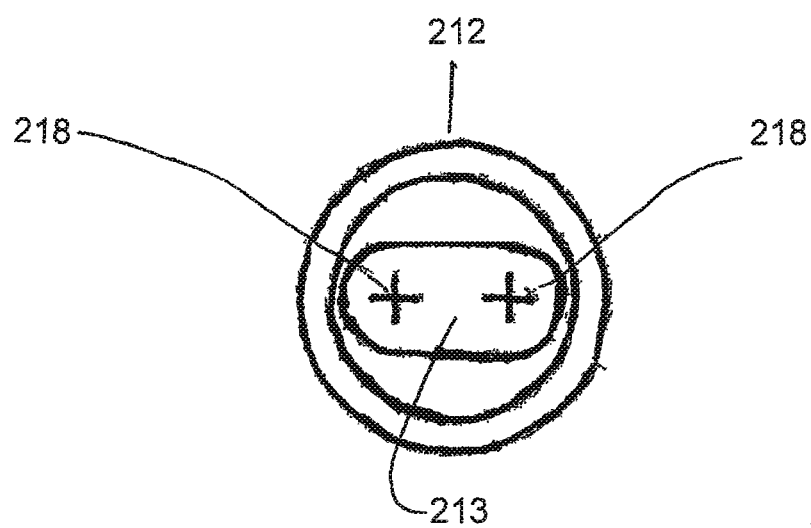
FIG. 26 illustrates a cross-section of an embodiment of a keyed eyelet cap.

In some embodiments, the eyelet cap 212 is keyed such that an appropriately sized delivery catheter 115 (not shown) couples with the eyelet cap 212 at a keyed bore 213 (see FIG. 26). Alternative deployment schemes would involve deploying the occlusive component within the left atrium while keeping the anchors restrained. The device would then be advanced until the cupped occlusive component apposes the ostium and then the anchors would be deployed. This deployment scenario would use methods described previously to load the device onto the delivery catheter 115.

In some embodiments the device is configured to be repositionable or retrievable after delivery to the site of the ostium of the left atrial appendage. A retrieval cord can be looped from the proximal end of the delivery catheter 115 through the lumen and through the proximal eyelet 114 and back through the membrane component 109 to continue back towards the proximal end of the delivery catheter 115 where the cord may be manipulated by an operator. Retrieval cords can be manufactured of any biocompatible material of sufficient strength and size. Such materials include fluoropolymers and expanded fluoropolymers and combinations thereof, such as expanded polytetrafluoroethylene (ePTFE). The retrieval cord can be used to aid in the repositioning of the device when the device is partially deployed. This can be accomplished by gentle traction on both ends of the retrieval cord at its exit from the proximal end of the delivery catheter 115. The retrieval cord can also be used to retrieve the device when the device has been fully deployed. A fully deployed device is a device which has been deployed or detached from the delivery catheter. The retrieval cord remains looped through the proximal eyelet 114 of the device during deployment and can be used to pull the entire device back into the delivery sheath 117 post-deployment, if necessary.

As shown in FIGS. 1 to 4 and in FIG. 6, a membrane component 109 is configured to inhibit passage of blood. Embodiments can provide a membrane component 109 configured to inhibit the passage of blood through the membrane, i.e., substantially occludes the flow of blood through the membrane. Some embodiments can provide a membrane component 109 that is configured to induce rapid tissue ingrowth and immediately or rapidly occludes the passage of blood through the membrane. In some embodiments, the membrane component 109 provides for a blood or body fluid impermeable membrane that occludes the flow of blood or bodily fluids through the membrane yet still promotes tissue ingrowth and endothelialization. Such embodiments can comprise a fluoropolymer such as an expanded polytetrafluoroethylene polymer. In some embodiments the inhibition of blood or bodily fluid passage across the membrane component 109 is immediate and does not rely on the thrombotic process. Membrane component 109 can also serve as a tissue ingrowth scaffold for durable occlusion and anchoring of the device. The microporous structure of the membrane component 109 can be tailored to promote tissue ingrowth and/or endothelialization. The membrane component 109 can be modified by various chemical or physical processes to enhance certain mechanical or physical properties. A hydrophilic coating can be applied to membrane component 109 to promote its wettability and echo translucency. Additionally, a physiochemical modification can be employed whereby the membrane component 109 includes chemical moieties that promote endothelial cell attachment, migration, and/or proliferation, or to resist thrombosis. A surface modified with covalently attached heparin is one non-limiting example of a membrane modification. In some embodiments the membrane is impregnated with one or more drug substances that are released in situ to improve healing response or reduce tissue inflammation. In some embodiments, the drug substance is selected from the group consisting of a corticosteroid, a human growth factor, an anti-mitotic agent, dexmethasone sodium phosphate, and an antithrombotic.

The membrane component 109 can be made of any biocompatible materials, including fluoropolymers such as polytetrafluoroethylene and expanded polytetrafluoroethylene;

polyesters; silicones; urethanes; or other biocompatible polymers and combinations thereof. Some embodiments comprise a membrane component comprising a fluoropolymer such as polytetrafluoroethylene or expanded polytetrafluoroethylene. In some embodiments, the membrane component comprises expanded polytetrafluoroethylene.

Some embodiments of the hub component 110 of the invention are constructed of a composite of nitinol wire and membrane. In some embodiments, the hub component 110 is constructed from wire. The construction of the composite embodiment of the hub component is detailed in a later example. Some embodiments of the device comprise a lumen 122 extending along or parallel to the central axis of the expandable frame. In some embodiments, the lumen can be sized to permit passage of about an 0.9 mm diameter guide wire to facilitate coaxial alignment within a body cavity, such as the left atrial appendage. The lumen passes through the proximal eyelet 114, the cupped occlusive component 104, the hub component 110, the anchor component, and the distal eyelet 113. A lumen 122 can be formed by winding wires around a center pin 22 to form a hollow central core through each of the following elements: proximal eyelet 114, the occlusive component 104, the hub component 110, the anchor component, and the distal eyelet 113. In some embodiments the lumen 122 permits fluoroscopic contrast injection behind the seated device to facilitate acute seal assessment.

Some embodiments of the hub component 110 can be constructed of multiple nitinol wire components held together with fluoropolymers such as expanded polytetrafluoroethylene (ePTFE) or various flexible fluoroelastomers. In some embodiments a multi-component structure held together with a flexible interposed element would permit articulation between the occlusion element and the anchoring element, thus potentially facilitating a safer, more stable and effective occlusion. In some embodiments the hub component 110 can be constructed of continuous wires, such as nitinol, with or without coverings.

Figure 5A:
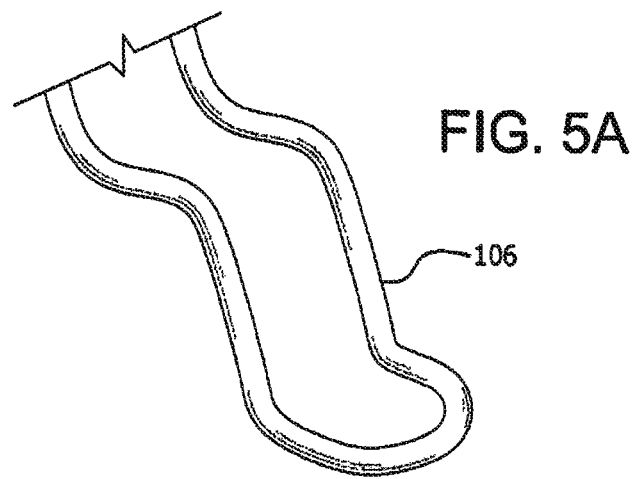
FIG. 5A illustrates a feature of an anchor of the device of FIG. 1.
Figure 5B:
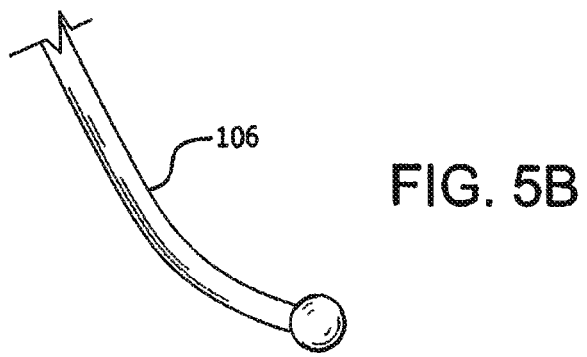
FIG. 5B illustrates an embodiment of an anchor of the device.
Figure 5C:
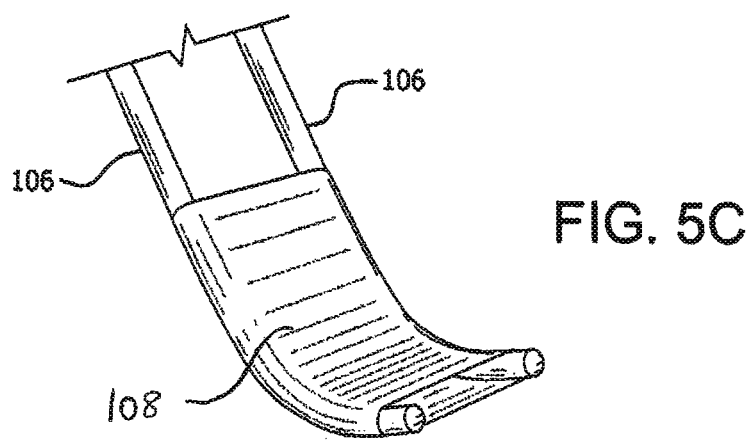
FIG. 5C illustrates an embodiment of an anchor of the device.

In some embodiments one or more anchors 106 consist of multiple wires that radiate outward or radially while extending distally and containing a small turn or bend directed proximally at the end of the anchor. In some embodiments the anchors 106 consist of looped wire (see FIGS. 1-4 and 6) or individual wire radiations (see FIGS. 5B and 5C). In some embodiments, the proximal turn of the loops can be formed approximately perpendicular to the angle of the outward radiation of the one or more anchors. In some embodiments one or more of the anchors 106 is bare. In some embodiments one or more of the anchors 106 is covered in whole or in part by a membrane 108. In some embodiments anchors are not substantially covered with a membrane (see, for example, FIG. 8). In some devices there are a combination of bare and covered/partially membrane covered anchors. In some embodiments membranes 108 of the looped anchors 106 prevent the anchor legs from becoming entangled during loading, deployment, retrieval and redeployment. In some embodiments, a membrane covering 108 is located around the proximal bend of the looped anchor 106. In some embodiments, the membrane covering 108 can provide for rapid tissue ingrowth and device stabilization. In some embodiments paired wire anchors 106 with a looped end 107 provide a device securing means that significantly reduces or prevents tissue perforation or piercing and the associated risk of pericardial effusion. In some embodiments the anchor element 106 with looped ends 107 is capable of secure anchoring due to the radial expansion force from the wire elastic property and the terminating proximal turn's ability to engage or hook the left atrial appendage wall and trabeculae. The looped end anchors 106 is likely capable of being recaptured and redeployed with significantly reduced trauma or damage to the device or to the surrounding tissue.

In some embodiments, anchors are NiTi wires. In some embodiments, the NiTi wires have a outer diameter from about 0.008" to about 0.013". In some embodiments, the overall length of the anchor is from about 0.13" to about 0.63". In some embodiments, the overall length of the proximal anchor turn is about 0.1" to about 0.2"

In some embodiments, anchors, barbs, or portions of anchors and barbs are constructed of a non-permanent biodegradable or bioabsorbable material which are resorbed over a period of time. In some embodiments the bioabsorbable nature of the anchors and barbs allows active acute fixation, facilitates ingrowth, and reduces the risk of undesired tissue or organ perforation.

In some embodiments, anchors and/or barbs have one or more bends at or near the connection point to the device. In some embodiments, the bend radius is between about 0.06" to about 0.2".

In some embodiments one or more of the anchors 106 is a single-wire anchor, i.e. non-looped wire, that radiates outward from the proximal central hub to a sharp point or atraumatic ball 145 on the terminating end. In some embodiments, one or more of the single leg anchors contain at least one dog-leg feature on the outward radiating wire element. In some embodiments the dog-leg feature facilitates anchor disengagement when a sheath is passed over it for recapture. In some embodiments, the distal end of an anchor having looped ends may be cut approximately at the apex of the loop to form a pair of single wire anchors (see FIG. 5C). In some embodiments, one or more anchors having looped ends have at least one dog-leg feature (see FIG. 5A). In some embodiments, one or more anchors have looped ends, and include two or more bends along the length of the anchor (see, e.g., FIG. 5A). In some embodiments the plurality of distinct radiating wire anchoring elements give the device an advantage because of the independence each anchoring element has from the other elements. Although not wishing to be bound by theory, it is postulated that this independence allows the anchors 106 to conform to the variable appendage anatomy while still maintaining secure anchoring.

In some embodiments, anchors include one or more hinge features. One or more hinges may be at or adjacent to a point at which the anchors connect to the distal portion of the device, or along the longitudinal length of the anchor. In some embodiments, the hinges provide for rotation of the distal portion of an anchor of at least about 0-90 degrees with respect to a proximal portion of the anchor. In some embodiments the hinge feature permits the anchors to better secure the device to the left atrial appendage.

Some embodiments have paired wire anchors 200 with a looped end 107 formed such that the shaft of the wire anchors 202 have adjacent wires that are substantially in contact prior to diverging toward the looped end 107 of the anchor. This configuration (shown in FIG. 23) would allow for reduced deployment and repositioning forces. These embodiments could also reduce the likelihood of anchor crosstalk or entanglement while loaded into a catheter prior to delivery. Some embodiments of looped wire anchors include a rounded loop end, a diamond shaped loop end, a pointed loop end, and a side by side loop end.

In some embodiments, the distance between the two legs of a looped wire anchor is greater at the base of the anchor than in a bend region of the anchor. In some embodiments a centerless grind process is employed to form the distance between the two legs of the anchor.

In some embodiments, the device 100 comprises two or more different forms of anchors 106. For example, in some embodiments, the device comprises one or more looped wire anchors and one or more single-wire anchors.

In some embodiments, the conformation of an anchor pre-heat setting is different from the conformation of the anchor post-heat setting.

Figure 25:
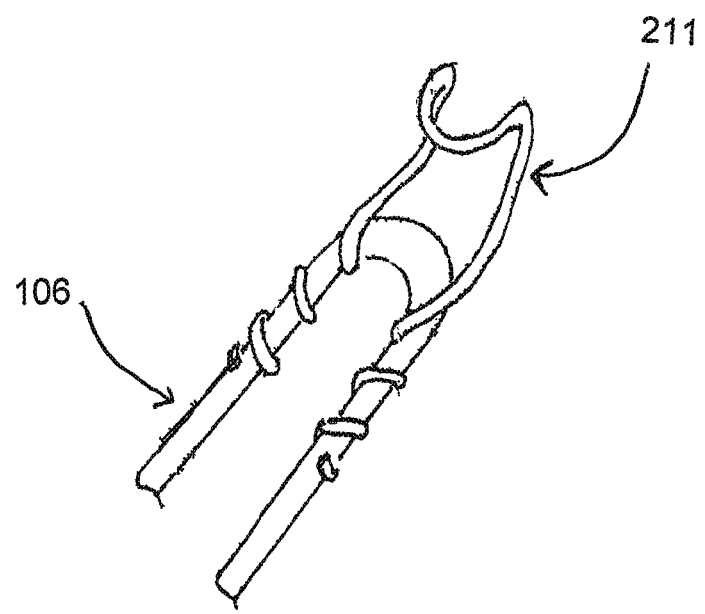
FIG. 25 illustrates an embodiment of an anchor.

In some embodiments, the anchor 106 further comprises at least one barb 211 affixed to or wrapped around the anchor (see FIG. 25). In some embodiments, at least one barb is substantially perpendicular to the angle of the outward radiation of the respective anchor. In some embodiments, the barb protrudes in a direction away from the general direction of the anchor. In some embodiments the barb is a smaller gauge wire than that of anchor 106. In some embodiments, the barb contains at least one dog-leg feature. In some embodiments, the barb terminates at a sharp point at its distal end. In some embodiments the barb terminates at its distal end as an atraumatic ball.

In some embodiments, the barb is fixed to or wrapped around the anchor at two or more points to form a loop. In some embodiments, the looped barbs include one or more (e.g., one, two, three, or more) bends, dog-legs, or hinges, or combinations of bends, dog-legs, and hinges.

It is understood that as the number of components on a device increases, it generally becomes progressively more difficult to deploy the device in a catheter sheath of limited size. Additionally, as barbs are sometimes positioned so as to extend away from an anchor in a direction not parallel to the longitudinal axis of the anchor, the barbs might become entangled with other barbs, anchors or other device components. Accordingly, in some embodiments, barbs are constructed including a bend or a hinge, such that the barb/tine is bent backwards along the axis of the anchor while present in the anchor sheath but are outwardly deployed when the device moves out of the catheter sheath.

In some embodiments, a barb is positioned on a leading portion of the anchor, i.e. on a portion of the anchor closer to the distal end of the device than to the proximal end of the device. In some embodiments, the barb located on the leading portion of the anchor is proximal-facing while in some embodiments, the barb located on the proximal end of the device faces the distal end of the device. In some embodiments, a proximal-facing barb is attached to a looped anchor while in some embodiments the proximal facing barb is attached to a single leg anchor.

Barbs can be designed so as to be compliant, non-compliant, or partially compliant and partially non-compliant. In some embodiments, some or all of a barb is covered or coated to prevent or limit tissue penetration. In some embodiments, the barb is covered or coated with suitable biocompatible materials including, but not limited to, fluoropolymers such as polytetrafluoroethylene and expanded polytetrafluoroethylene; polyesters; silicones; urethanes; or other biocompatible polymers or combinations thereof. In some embodiments, the coated- or covered-barb provides a structure and substrate for tissue ingrowth around the barb. In some embodiments the coating or covering on the barb provides protection against entanglement of adjacent anchors and/or barbs. In some embodiments, barbs are coated/covered with a material which minimizes friction against the catheter wall, thereby aiding deployment and/or retrieval of the device. In some embodiments, a barb having one or more sharp tips is coated/covered such that only limited tissue penetration is permitted. In some embodiments, the covering of the barb is impregnated with one or more drug substances which are released in situ to improve healing response or reduce tissue inflammation. In some embodiments, the drug substance is selected from the group consisting of a corticosteroid, a human growth factor, a anti-mitotic agent, dexmethasone sodium phosphate, and an antithrombotic.

In some embodiments, anchors 106 are formed from strands of twisted or braided wires. In some embodiments barbs on such anchors are formed by cutting one or pulling away one or more strands of the twisted or braided wire from the twisted or braided wire.

In some embodiments, the anchors and/or barbs include a textured surface to aid in securing the device to surrounding tissue.

In some embodiments, one or more anchors each includes two or more structures selected from bends, dog-legs, hinges, barbs, and surface texturing.

In some embodiments the radial arrangement of the anchors is staggered according to anchor feature (for example, by overall anchor length (e.g. long-short-long-short)). In some embodiments, the radial arrangement of the anchors is biased according to anchor feature (for example, by configuration (e.g. looped wire anchor-single leg anchor-looped wire anchor-single leg anchor)).

In some embodiments, anchors are spaced uniformly apart, i.e. each anchor 106 is equally spaced radially about the circumference of the distal portion of the device.

In some embodiments the anchor 106 exits the proximal central hub of the device at an angle substantially perpendicular to the longitudinal axis of the device. In some embodiments the anchor 106 exits the device at an angle between 20-80 degrees compared to the longitudinal axis of the device, wherein the distal point of the anchor extends to, and potentially past, the distal eyelet.

In some embodiments, each of the one or more anchors is substantially identical, i.e. each anchor has about the same overall length, the same planar arrangement (i.e. having similar absence or presence of one or more dog-leg features; presence or absence of one or more hinges), the same radial angle with respect to the longitudinal axis of the device (axis formed between distal and proximal end of the device), and the same configuration (for example, a looped end anchor, a twisted wire end, or a single-wire anchor). In some embodiments, one or more of the anchors differs from at least one other anchor with respect to at least one of overall length, planar arrangement, radial angle, or configuration.

Figure 24:
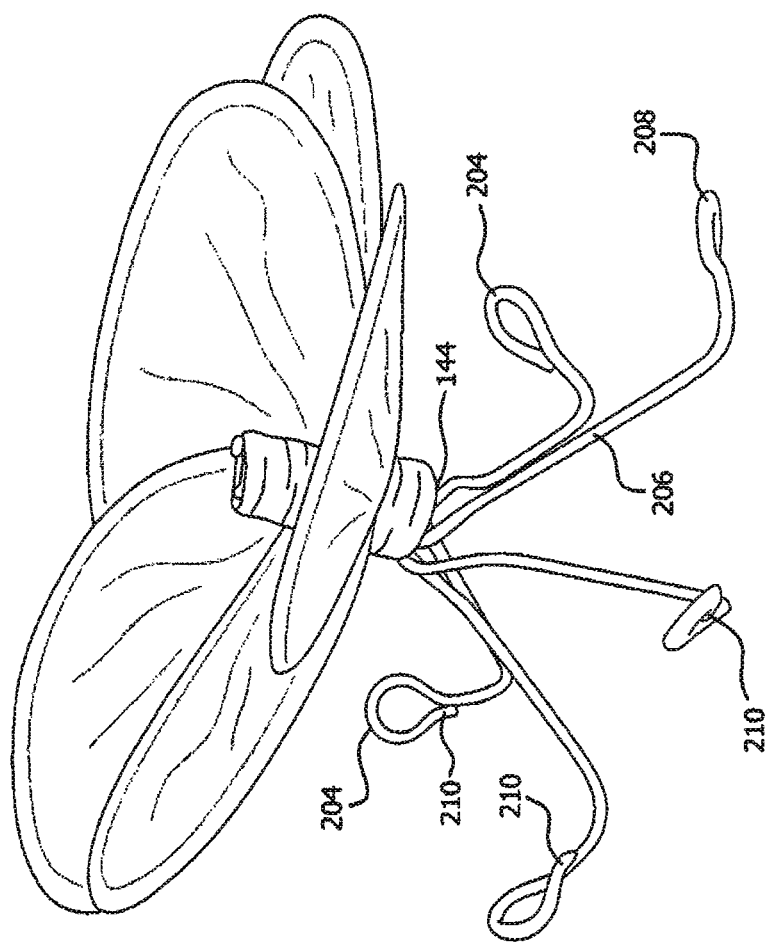
FIG. 24 illustrates an embodiment of an anchor.

Some embodiments as shown in FIG. 24 have single-leg anchors 204. Anchors 204 can be formed from the same wires that form the eyelet 144, in various embodiments. Anchor 204 comprises a shaft portion 206, a rounded portion 208 and a wire end 210. The wire end 210 can be configured to twist or protrude away from the plane of rounded portion 208 to serve as barbs or protrusions for further anchoring.

Some embodiments provide a looped wire anchor 106 with a barb 211 attached to the anchor at multiple sites (shown in FIG. 25).

In some embodiments the anchor wires protrude from the device at a hub flange. In some embodiments, the hub flange is covered with a compliant hub extension made as an overmold or as a pre-molded component.

Figure 27A:
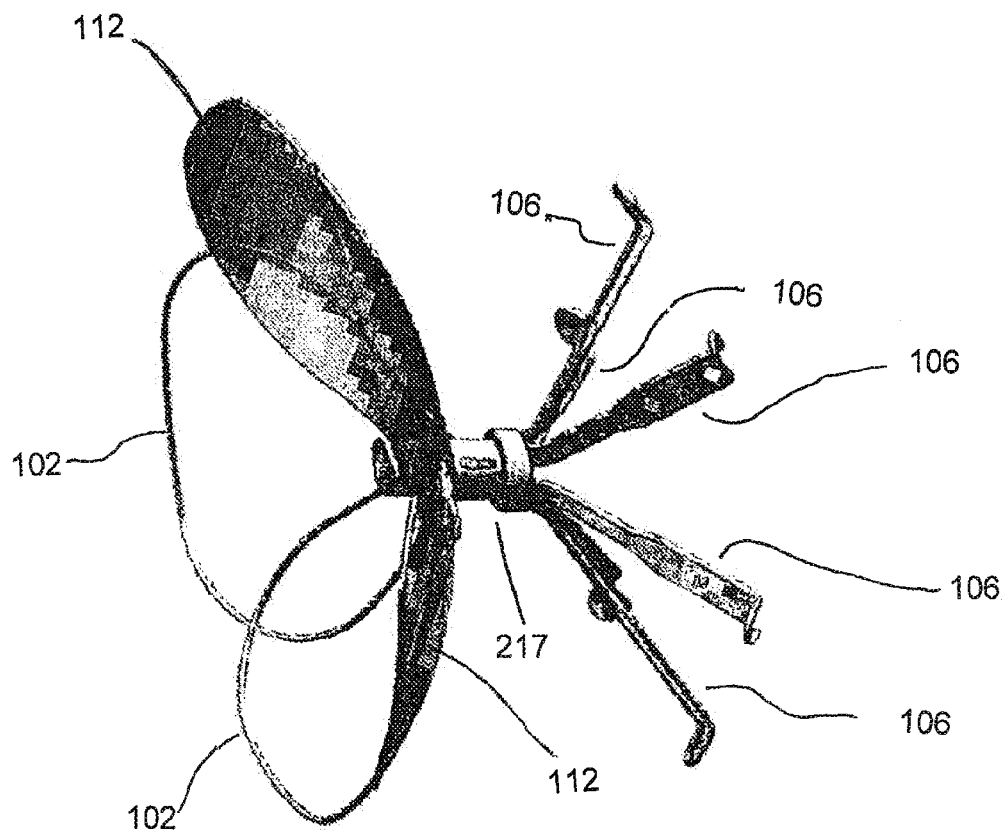
FIG. 27A shows a perspective view of an embodiment of the device using a modular anchoring component.
Figure 27B:
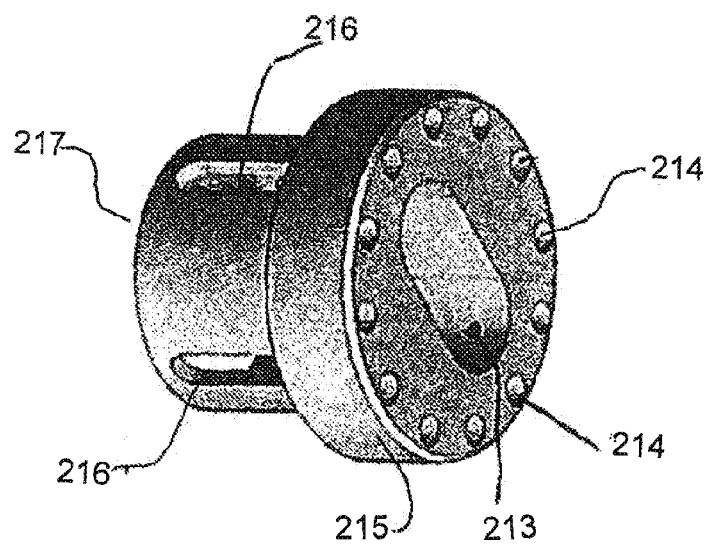
FIG. 27B shows an expanded view of a modular anchoring hub component.

An exemplary embodiment of the device is shown in FIG. 27A and includes a modular anchoring hub 217 that connects anchors 106 to the occluding device (including petals 112 supported by expandable frame 102) wherein anchors 106 are axially mounted into a flange 215 (shown in FIGS. 27B and 27B). Such a modular anchoring hub allows rapid customization of the type of occluding device as well as the type and format of the anchors and can allow optimization of the device based on selection criteria including desired occlusive device, desired anchoring mechanism, and size and anatomy of the left atrial appendage. In some embodiments, the modular anchoring component reduces the profile of the distal end of the device and therefore minimizes potential for thrombus formation.

In some embodiments, the modular anchoring component is attached directly to the occlusion device or is attached to the occlusion device via a flexible connector. In some embodiments, the modular anchoring component permits different arrangements of anchors. For example, in some embodiments the modular anchoring component permits the anchoring of single-leg type anchors, looped wire anchors, and combinations of single-leg and looped wire anchors. In some embodiments, the axial attachment of the anchors to the modular anchoring component allows a reduction in device profile and reduced deployment and retrieval forces in the delivery catheter.

In some embodiments, the modular anchoring hub also allows for a variety of anchor configurations (e.g. active or passive geometries, anchor number, anchor size, anchor distribution and anchor length, and anchor mounting to hub). In some embodiments, the legs of an looped wire anchor are adjacent to one another, i.e. in an adjacent configuration In some embodiments, legs of a first looped wire anchor are separated from one another by the leg of an adjacent looped wire anchor, i.e. in a staggered configuration Although not wishing to be bound by theory, it is thought that an adjacent configuration allows more side to side movement of the anchors while minimizing interference between adjacent anchors, and that a "staggered" configuration provides wider support at the hub, minimizes side to side movement of the anchors, and due to interference between adjacent anchors, provides further side to side support.

In some embodiments, the device further comprises keyed eyelet caps to engage an appropriately keyed delivery catheter. In some embodiments the keyed bore 213 accepts the end of a flattened delivery catheter. In some embodiments, suture holes 218 permit the passage of a looped suture from the catheter around the eyelet cap so as to secure the device to the catheter. In some embodiments, the thread axis is offset from the eyelet axis so as to reduce rotational torque to device generated during release.

In some embodiments, eyelet caps comprise a sleeve and an end cap, each made of nitinol or other appropriate material. Sleeves are disposed around the eyelet and, in some embodiments, are welded or adhered to the eyelet. In some embodiments, the sleeves includes one or more slots radially arranged around the sleeves, each slot extending down the sleeve along the axis of the device. In some embodiments, the slot provides access for welding and/or adhesive bonding. In some embodiments, the sleeves engage each of the frame wires and assist in maintaining a desired spacing between the frame wires.

In some embodiments, the sleeves are added during device assembly, prior to bag attachment with the end cap added at the end of assembly. In some embodiments, the end cap is attached to the sleeve with a snap-in assembly wherein one or more tabs on the sleeve engage with a flange on the end cap. In some embodiments the tabs and flange are aligned so as to confirm proper alignment and calibration between proximal and distal eyelets.

Some embodiments include an overmold of a suitable plastic material (e.g. thermoplastic or a fluoropolymer) over the sleeves. In some embodiments the overmold includes one or more lightly grooved areas for bag attachment.

In some embodiments, the device is optimized to have a particular occlusive disk diameter to device length ratio. In some embodiments the ratio of occlusive disk diameter to the length of the device is between 1:2 and 2:1. In some embodiments, the disk diameter to device length ratio is 1:1. In some embodiments the waist length of the device (e.g. the distance between the distal aspect of the proximal occlusive disk and origination of the anchor projections) is adjusted so as to yield the desired ratio.

Figure 9:
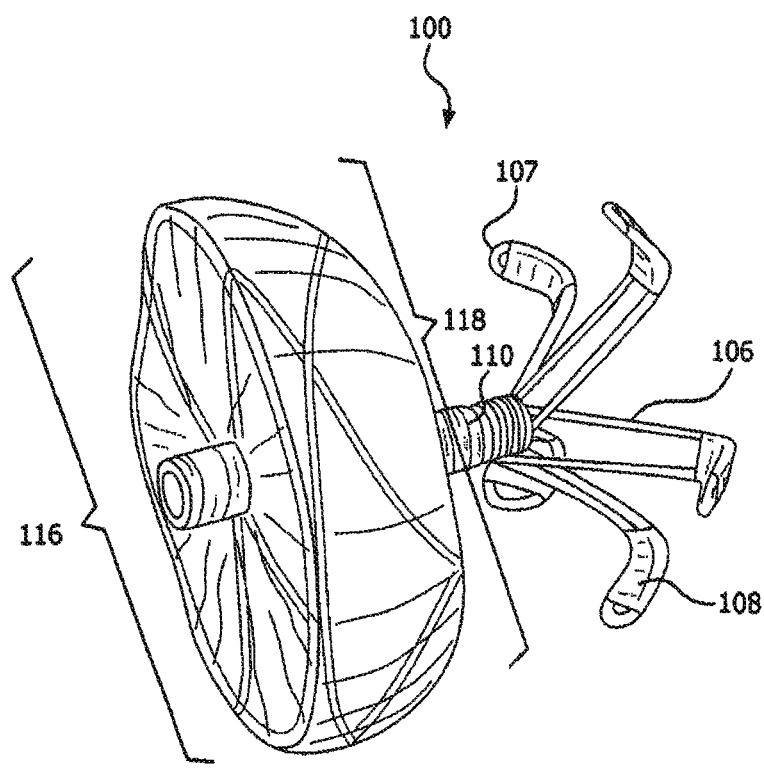
FIG. 9 provides a perspective illustration of an embodiment of the device.
Figure 10A:
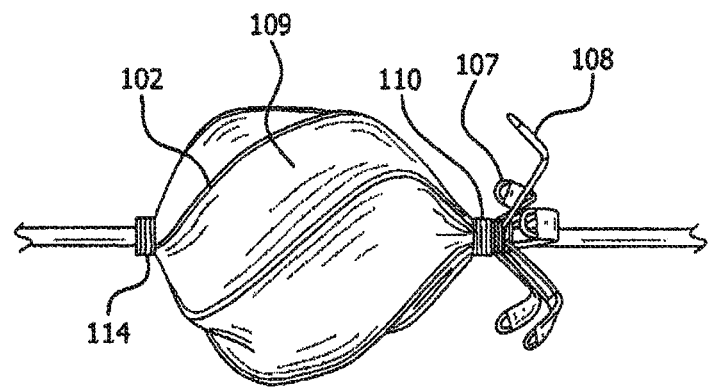
FIGS. 10A and 10B illustrate two embodiments of related devices as they would appear extended on a mandrel.
Figure 10B:
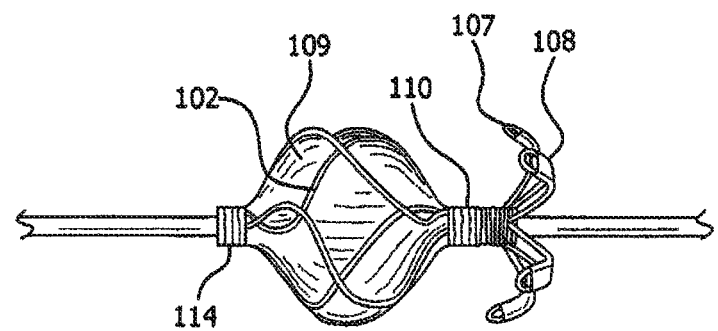

As shown in FIG. 9, some embodiments provide a membrane component configured to inhibit passage of blood and an expandable frame formed from a plurality of wires having a cupped occlusive component with a flat proximal surface 116 and a cupped distal surface 118 at least partially covered with the membrane component 109, one or more anchors 106 with looped ends 107 and a hub component 110. Such a configuration can permit deeper, more secure seating within the left atrial appendage ostium while still eliminating the residual left atrial appendage stump that could be a source of thrombus or blood clot formation.

Example 1

An about 1 meter length of 10% platinum drawn filled nitinol wire (Fort Wayne Metals, Fort Wayne, Ind.) with a diameter of about 0.23 mm is obtained. The specific length of the wire may or may not be measured, but the wire should be long enough to complete the winding pattern as described in the following paragraph. The wire is obtained having been electropolished. Electropolishing nitinol wire imparts certain well known properties, such as spontaneously forming a titanium dioxide layer on the surface, selectively reducing the amount of nickel on the surface of the wire, and removing some of the stresses in the wire thus improving fatigue.

Figure 11:
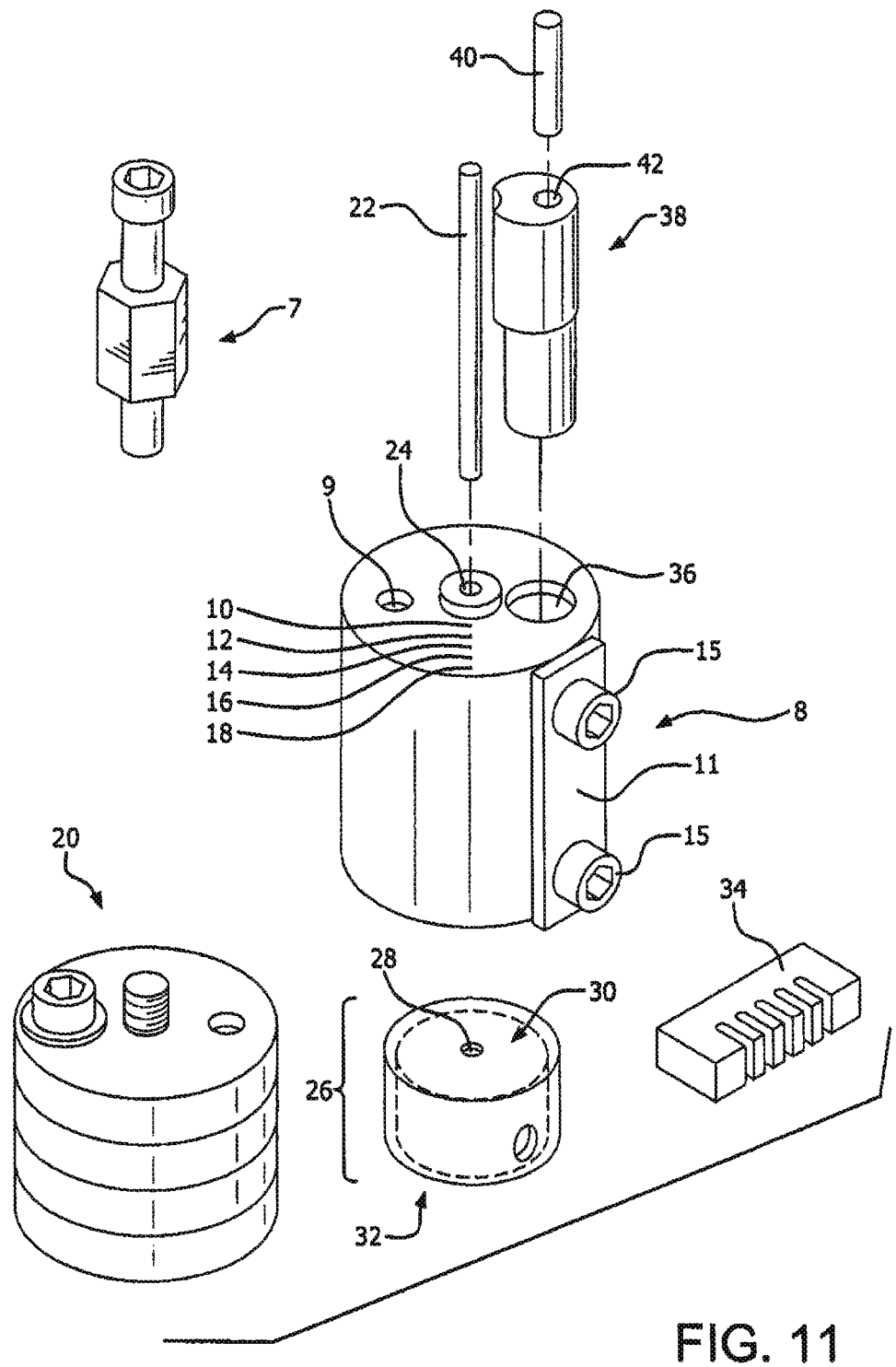
FIG. 11 illustrates wire forming tooling for manufacturing embodiments.

A base jig 8 as described in FIG. 11 is obtained. A knot is tied into one end of one length of an about 0.5 meter long wire and the unknotted end is fed through a wire feed hole 10. Two additional lengths of wire (about 1 meter each) are folded in half and the free ends are fed through the remaining four feed holes 12, 14, 16, 18, with the wire entering the holes at funnel-shaped opening 19 with the small feed holes at the bottom of opening 19. The wires then exit through holes 10, 12, 14, 16 and 18 at the flat end surface of jig 8. Weights 20 are attached to the free ends of the five wires to hold the wires taut and in place. The base jig is secured in a chuck of a lathe and center pin 22 is inserted into center pin hole 24 far enough to securely seat it.

The other end of center pin 22 is located inside the center hole 28 of tail stock support 26 which is chucked into the tail stock, wherein the closed face 30 of the tail stock support 26 faces the base jig 8. The base jig 8 and tail stock support 26 are positioned about 5 cm apart. A wire guide 34 is used to prevent the wires from crossing. The base jig 8 is positioned so that the wire feed holes 10, 12, 14, 16, 18 are oriented vertically above the center pin 22 and the wires are positioned on the trailing side of the center pin 22.

The petal jig hole 36 is rotated 720 degrees (deg.). The petal jig 38 is inserted into the petal jig hole 36. Without crossing the wires, the wires are placed on top of the petal jig 38. The base jig 8 is rotated 360 deg to create the petals of the device. The base jig 8 is rotated another 720 deg with the wires placed on top of the center pin 22 in order to create the center eyelet.

The anchor pin 40 is next inserted into the anchor pin hole 42. The wires are then looped around the anchor pin 40 and the base jig is rotated 720 deg in order to form the distal eyelet. The wire pivot 7 is inserted into wire pivot hole 9. The wires are fed around the wire pivot 7 and placed under anchor plate 11. The anchor plate 11 is secured with Allen head screws 14. The wires are cut on the weight 20 side of the anchor plate 11.

With the weights 20, the tail stock support 26, and the wire guide 34 removed, the assembly can be placed in a convection oven set to 475 deg C. for 14 minutes, for example. The assembly is removed from the oven and quenched in water. The jigs are disassembled and the article is removed.

The wire ends are trimmed to the eyelets and the petals are fanned in the same direction as the helical winding, such that each petal is oriented 72 degrees offset relative to the adjacent petal. As a consequence of the fanning of the petals, the anchor loops are also fanned.

Figure 12B:
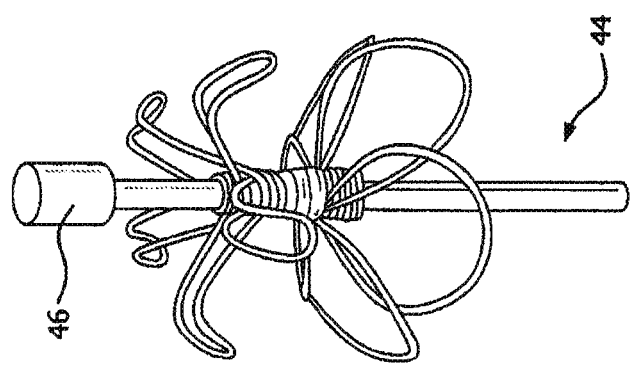
FIG. 12B provides a perspective of a heat set mandrel used in the manufacture of an embodiment of the device.
Figure 12A:
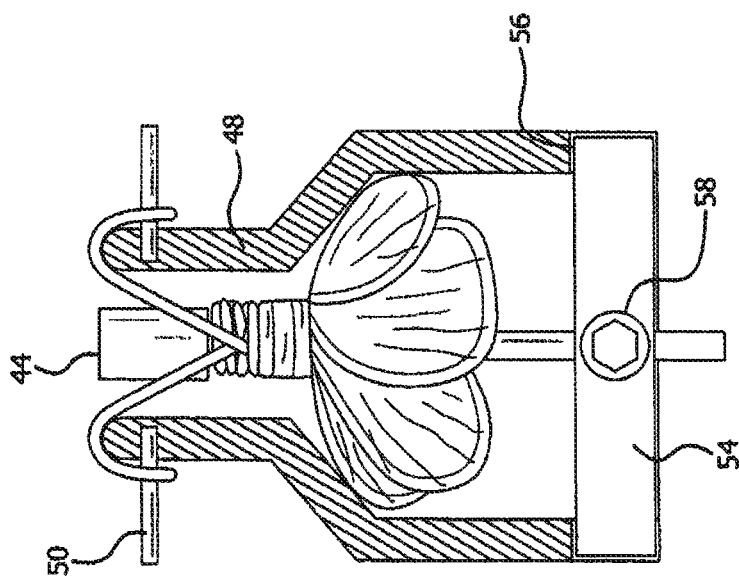
FIG. 12A shows a cut away view of a heat set tool used in the manufacture of an embodiment of the device.
Figure 12C:
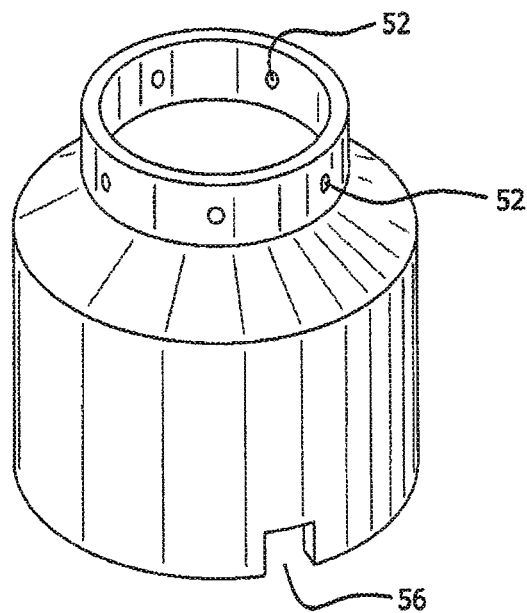
FIG. 12C shows an exterior of a heat set tool used in the manufacture of an embodiment of the device.
Figure 12D:
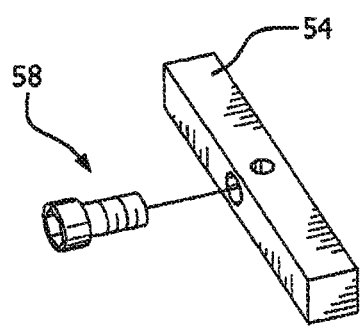
FIG. 12D shows a cross bar for utilization with a heat set tool used in the manufacture of an embodiment of the device.

A heat set mandrel 44 is obtained as described in FIG. 12B. The article is placed onto the heat set mandrel such that the cap 46 is positioned adjacent to the anchor loops. The article is then placed inside the heat set tool 48 (see FIGS. 12A and 12C) such that the petals are positioned inside a heat set tool and the anchor loops protruded over the lip of the heat set tool 48. Anchor loop pins 50 are inserted through the anchor loops and secured in the anchor pin holes 52. The heat set mandrel 44 is inserted onto the center hole of cross bar 54 (FIG. 12D) and the cross bar 54 is seated into the notches 56 of the heat set tool 48. The heat set mandrel 44 is forced into the heat set tool 48 to achieve the desired angles of the anchors and the mandrel is then locked in place using the set screw 58.

The assembly is placed in a convection oven set to 475 deg for 5 and transferred to a 2 mm mandrel.

Figure 13:
FIG. 13 shows a perspective view of a mandrel used in the attachment of the membrane component manufacture of the device.
Figure 14:
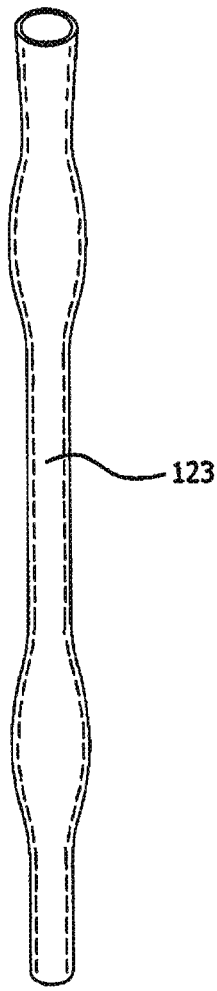
FIG. 14 shows a perspective view of a mandrel used in the attachment of the membrane component manufacture of the device.

While maintaining the petal orientation, the article is powder coated with FEP powder (obtained from in house stock) in the following manner. A 2 mm outer diameter mandrel with a length sufficient to be inserted into the blender described further in this paragraph is obtained. The mandrel 123 is flattened by crimping at two locations spaced about 2.5 cm apart. See FIGS. 13 and 14. The mandrel 123 is inserted into the center hole of the article. One end of the mandrel 123 is grounded. A commercial blender (Variable Speed Lab Blender, Waring, Torrington, Conn.) is obtained and a quantity of FEP powder is added, leaving the tip of the blender blades exposed. The article and mandrel are suspended in the center of the blender, the lid is replaced, and the blender is turned on to the highest setting for about 5 seconds. The article and mandrel 123 are removed, the mandrel is tapped to achieve a more uniform powder coating, and the article and mandrel 123 are then hung inside a convection oven set to 320 deg C. for 3 minutes. The article and mandrel 123 are removed from the oven, allowed to cool, and the mandrel is removed. The excess FEP is cleaned from the mandrel, and the mandrel is reinserted into the article.

The article is extended in length on the mandrel 123 by grasping the proximal and center eyelets with tweezers. The eyelets are fixed in place by positioning them beyond the crimps in the mandrel.

A porous ePTFE film having the following properties is obtained:
  Methanol bubble point of 0.7 psi
  Mass/area of 2.43 grams/square meter
  Longitudinal matrix tensile strength of 96000 psi
  Matrix tensile strength in the orthogonal direction of 1433 psi
  Longitudinal maximum load of 1.6 kg/inch
  Thickness of 0.00889 mm Methanol bubble point is measured using a custom built machine with a 1 inch diameter foot, a ramp rate of 0.2 psi/second and a liquid media of methanol. Length and width of the material are measured using a metal ruler. Mass/area is measured using a balance (Model GF-400 Top Loader Balance, ANG, San Jose Calif.) with a 36×5 inch sample. Longitudinal maximum load is measured using a materials test machine (Model 5564, Instron, Grove City, Pa.) equipped with a 10 kg load cell. The gauge length is 1 inch and the cross head speed is 25 mm/minute. Sample width is 1 inch. Longitudinal tensile test measurements are taken in the length direction of the material. Thickness is measured using a thickness gauge (Mitutoyo Digital Indicator 547-400) with a foot diameter of ⅝ inch. The longitudinal matrix tensile strengths (MTS) are calculated using the following equation:

$$\text{Matrix Tensile Strength} = \frac{(\sigma_{sample}) * (\rho_{PTFE})}{(\rho_{sample})}$$

where:

$\rho_{PTFE} = 2.2$ grams/cc $\sigma_{sample} = $ (Maximum Load/Width)/Thickness $\rho_{sample} = $ (Mass/Area)/Thickness Density is calculated using the formula, density=mass/volume.

A 30 mm film tube is constructed from the ePTFE material in the following manner. For a 25 mm diameter device, a film with a slit width of about 1.905 cm is wound on a 30 mm OD mandrel. The amount of film overlap is not critical but preferably there will be at least some overlap of the edges. The tube is then removed from the mandrel and stretched to make the ID of the tube to be about 25 mm.

The film tube is slipped over the tensioned article and using ePTFE film, the ends of the tube are cinched around the two eyelets.

Another porous ePTFE film, having a layer of FEP, is obtained having the following properties:
  Mass/area of 36.1 grams/square meter
  Maximum Load, Longitudinal of 12.6 kg/inch
  Maximum Load, Transverse of 0.3 kg/inch
  Thickness of 0.0012 inch Test methods for the above tests are described previously. The FEP thickness in the film is about 62.5%. FEP thickness (%) is calculated as ratio of the FEP thickness and the film thickness. The reported value represents the average measurements for five samples. FEP thickness and film thickness is measured from scanning electron microscope images of cross sections of the ePTFE/FEP laminate material in the following manner. The magnification is chosen to enable the viewing of the entire film thickness. Five lines perpendicular to the horizontal edge of the image are randomly drawn across the full thickness of the film. Thickness is determined by measuring the thickness of the FEP and the thickness of the film.

A 2 mm wide strip of this FEP-coated ePTFE film, with the FEP side down, is wrapped four times around the cinched portions and heated with a soldering iron to bond the film layers together.

A tubular, porous expanded polytetrafluoroethylene tube having a 1.279 mm ID and an 1.452 mm OD is obtained. It possessed the following properties:
  Density of 0.531 g/cc
  Matrix tensile strength in the longitudinal direction of 34215 MPa
  Thickness of 0.086 mm.

About 4 mm lengths of this tube are placed over each anchor and positioned as shown in FIGS. 1-3 and FIG. 7.

The article and mandrel are placed inside a convection oven set to 320 deg C. for 3 minutes and then removed and allowed to cool. The excess ePTFE material is trimmed.

Example 2

An article is constructed in the same manner, using the same materials, as Example 1 with the following exceptions. The film tube is not applied as a tube, but rather it is slit longitudinally and the resulting flat sheet is used to cover the nitinol frame. Without tensioning the occlusive member, the sheet is draped over the top frame petals and the edges of the sheet are gathered and secured around the center eyelet. The occlusive component of the resulting article has a cupped occlusive component with a flat proximal surface and a cupped distal surface as shown in FIG. 9.

Example 3

An article is constructed in the same manner, using the same materials, as Example 1 with the following exceptions. The cupped occlusive member and the anchor component are detached from each other by clipping the center eyelet by hand. An ePTFE tube with a diameter similar to that if the outer diameter of the eyelet shown in FIGS. 19A-19B is procured and secured to the distal eyelet of the cupped occlusive member and the proximal eyelet of the anchor component. The tube is secured by overwrapping tape containing FEP as previously described.

Example 4

An article is constructed in the same manner, using the same materials, as Example 1 with the following exceptions. The cupped occlusive member and the anchor component are detached from each other by clipping the center eyelet by hand. A ePTFE tube with a diameter similar to that if the outer diameter of the eyelet shown in FIGS. 19A-19B is procured and secured to the distal eyelet of the cupped occlusive member and the proximal eyelet of the anchor component. The tube is secured by applying Loctite 4011 adhesive to the outside diameter of each resulting eyelet and securing the ePTFE tube over the eyelets until cured.

Example 5

An article is constructed in the same manner, using the same materials, as Example 1 with the following exceptions. The cupped occlusive member and the anchor component are detached from each other by clipping the center eyelet by hand. A ePTFE tube with a diameter similar to that if the outer diameter was formed from ePTFE film as described previously. The tube is secured to the distal eyelet of the cupped occlusive member and the proximal eyelet of the anchor component. The assembly was then heated at 320 degrees C. for 3 minutes allowing the tube to shrink and securing it to the eyelets.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles described herein, to the full extent indicated by the broad, general meaning of the terms in which the appended claims are expressed. To the extent that these various modifications do not depart from the spirit and scope of the appended claims, they are intended to be encompassed therein.

What is claimed is:

1. An occlusive device comprising:
    a membrane component configured to inhibit passage of blood;
    an expandable frame having a distal end and a proximal end;
    a cupped occlusive component fully covered by the membrane component;
    one or more anchors located at or near the distal end of said expandable frame; and
    a hub component disposed between, and connected to, said occlusive component and said one or more anchors;
    wherein said expandable frame including said anchors is formed from a plurality of wires extending from the proximal end to the distal end of said frame;
    wherein at least one of said anchors includes a first leg and a second leg substantially parallel to each other and wherein the first leg and the second leg converge at an end of the anchor to form a barbless loop; and
    wherein at least one of said anchors is at least partially covered by a membrane covering.

2. An occlusive device according to claim 1, wherein said cupped occlusive component has a first configuration upon application of tensile force and a second configuration upon release of said tensile force, wherein said first configuration is a tube and said second configuration is a cupped shape formed from at least two overlapping petals configured to allow movement between the at least two overlapping petals.

3. An occlusive device according to claim 1, wherein the membrane component comprises fluoropolymer.

4. An occlusive device according to claim 3, wherein the membrane component comprises polytetrafluoroethylene.

5. An occlusive device according to claim 4, wherein the membrane component comprises expanded polytetrafluoroethylene.

6. An occlusive device according to claim 1, wherein the plurality of wires comprise nitinol.

7. An occlusive device according to claim 1, wherein at least one of said anchors extends away from the device in a generally distal direction and includes a first end in contact with the device and a second end.

8. An occlusive device according to claim 7, wherein the at least one of said anchors is a single-leg anchor.

9. An occlusive device according to claim 7, wherein the at least one of said anchors includes a bend near the second end of the anchor, and wherein the bend causes the second end of the anchor to be generally proximal-facing.

10. An occlusive device according to claim 7, wherein the at least one of said anchors includes a bend near the second end of the anchor, and wherein the bend causes the second end of the anchor to be generally distal-facing.

11. An occlusive device according to claim 7, wherein the at least one of said anchors includes one or more dog-leg features.

12. An occlusive device according to claim 7, wherein the at least one of said anchors includes one or more hinges.

13. An occlusive device according to claim 1, wherein the one or more anchors includes a plurality of anchors uniformly disposed radially about the device.

14. An occlusive device according to claim 1, wherein the one or more anchors includes a plurality of anchors disposed radially about the device such that adjacent anchors are substantially equally spaced from one another for all pairs of adjacent anchors of the radially disposed plurality of anchors.

15. An occlusive device according to claim 1, wherein the one or more anchors includes at least one single-leg anchor and at least one anchor having a first leg and a second leg, wherein the first leg and the second leg converge to form a loop.

16. An occlusive device according to claim 1, wherein the one or more anchors comprises a bioabsorbable material.

17. An occlusive device according to claim 1, wherein the one or more anchors comprises a biodegradable material.

18. An occlusive device according to claim 1, wherein the one or more anchors comprises a barb that includes a biodegradable or bioabsorbable material.

19. An occlusive device according to claim 1, wherein the membrane component comprises a biodegradable or bioabsorbable material.

20. An occlusive device according to claim 1, wherein the one or more anchors are arranged about the device in a staggered arrangement.

21. An occlusive device according to claim 1, wherein said hub component couples the cupped occlusive component to the one or more anchors.

22. An occlusive device according to claim 1, further comprising a flexible connector that is attached at a first end of the flexible connector to the cupped occlusive component and is attached at a second end of the flexible connector to the hub component, and wherein the one or more anchors are attached to the hub component.

23. An occlusive device according to claim 1, wherein the expandable frame includes an eyelet, and further comprising a cap component disposed over the eyelet, the cap component defining a bore configured to couple with a delivery catheter.

24. An occlusive device according to claim 23, wherein the bore of the cap component is keyed to couple with a mating portion of a keyed delivery catheter.

25. An occlusive device comprising:
a membrane component configured to inhibit passage of blood;
an expandable frame having a distal end and a proximal end;
a cupped occlusive component having a distal end and a proximal end;
one or more anchors; and
a hub component configured as a flexible connector between said occlusive component and said one or more anchors;
wherein said cupped occlusive component is fully covered by said membrane component and is formed from a plurality of wires extending from the proximal end of said cupped occlusive component to the distal end of said cupped occlusive component, and wherein at least one of said anchors includes a first leg and a second leg substantially parallel to each other and wherein the first leg and the second leg converge at an end of the anchor to form a barbless loop; and
wherein at least one of said anchors is at least partially covered by a membrane covering.

26. An occlusive device according to claim 25, wherein said cupped occlusive component has a first configuration upon application of tensile force and a second configuration upon release of said tensile force, wherein said first configuration is a tube and said second configuration is a cupped shape formed from at least two overlapping petals configured to allow movement between the at least two overlapping petals.

27. An occlusive device according to claim 25, wherein the membrane component comprises fluoropolymer.

28. An occlusive device according to claim 27, wherein the membrane component comprises polytetrafluoroethylene.

29. An occlusive device according to claim 28, wherein the membrane component comprises expanded polytetrafluoroethylene.

30. An occlusive device according to claim 25, wherein the plurality of wires comprise nitinol.

31. An occlusive device according to claim 25, wherein said flexible connector is one or more wires formed into a spring.

32. An occlusive device according to claim 25, wherein said flexible connector comprises a beaded chain.

33. An occlusive device according to claim 25, wherein said flexible connector comprises a coil type flexible connector.

34. An occlusive device according to claim 25, wherein said flexible connector comprises beads formed of braided wire.

35. An occlusive device according to claim 25, wherein said flexible connector comprises a flexible tube.

36. An occlusive device according to claim 35, wherein the flexible tube comprises ePTFE.

37. An occlusive device according to claim 25, wherein said flexible connector comprises silicone.

38. An occlusive device according to claim 37, wherein the silicone includes reinforcing members.

39. An occlusive device according to claim 25, wherein said flexible connector comprises a universal joint.

40. An occlusive device according to claim 25, wherein said flexible connector comprises a compressed spring.

41. An occlusive device according to claim 25, wherein at least one of said anchors extends away from the device in a generally distal direction and includes a first end attached to the device and a second end.

42. An occlusive device according to claim 41, wherein the at least one of said anchors includes a bend near the second end, and wherein the bend causes the second end to be generally proximal-facing.

43. An occlusive device according to claim 41, wherein the at least one of said anchors includes a bend near the second end, and wherein the bend causes the second end to be generally distal-facing.

44. An occlusive device according to claim 41, wherein the at least one of said anchors includes one or more dog-leg features.

45. An occlusive device according to claim 41, wherein the at least one of said anchors includes one or more hinges.

46. An occlusive device according to claim 25, wherein the one or more anchors includes a plurality of anchors uniformly disposed radially about the device.

47. An occlusive device according to claim 25, wherein the one or more anchors includes a plurality of anchors disposed radially about the device such that adjacent anchors are substantially equally spaced from one another for all pairs of adjacent anchors of the radially disposed plurality of anchors.

48. An occlusive device according to claim 25, wherein the one or more anchors includes at least one single-leg anchor and at least one anchor having a first leg and a second leg, wherein the first leg and the second leg converge to form a loop.

49. An occlusive device comprising:
a membrane component configured to inhibit passage of blood;
an expandable frame having a distal end and a proximal end;
a cupped occlusive component having a first configuration upon application of tensile force and a second configuration upon release of said tensile force;
one or more anchors; and
a hub component between said occlusive component and said one or more anchors;
wherein said cupped occlusive component is fully covered by said membrane component;
wherein said first configuration of said cupped occlusive component is a tube and said second configuration is a cupped shape formed from at least two overlapping petals configured to allow movement between the at least two overlapping petals;
wherein said expandable frame is formed from a plurality of wires extending from the proximal end to the distal end of said frame,
wherein at least one of said anchors includes a first leg and a second leg substantially parallel to each other and wherein the first leg and the second leg converge at an end of the anchor to form a barbless loop; and
wherein at least one of said anchors is at least partially covered by a membrane covering.

50. An occlusive device comprising:
a membrane component configured to inhibit passage of blood;
an expandable frame having a distal end and a proximal end;
a cupped occlusive component having a first configuration upon application of tensile force and a second configuration upon release of said tensile force;
one or more anchors; and
a flexible connector between said occlusive component and said one or more anchors;
wherein said cupped occlusive component is fully covered by said membrane component;
wherein said first configuration of said cupped occlusive component is a tube and said second configuration is a cupped shape formed from at least two overlapping petals configured to allow movement between the at least two overlapping petals; and
wherein said expandable frame is formed from a plurality of wires extending from the proximal end to the distal end of said frame,
wherein at least one of said anchors includes a first leg and a second leg substantially parallel to each other and wherein the first leg and the second leg converge at an end of the anchor to form a barbless loop; and
wherein at least one of said anchors is at least partially covered by a membrane covering.

* * * * *